US012121223B2

(12) United States Patent
Inglis et al.

(10) Patent No.: US 12,121,223 B2
(45) Date of Patent: *Oct. 22, 2024

(54) MULTIFUNCTIONAL VISUALIZATION INSTRUMENT

(71) Applicant: Covidien AG, Neuhausen am Rheinfall (CH)

(72) Inventors: Peter Douglas Colin Inglis, Boulder, CO (US); Hua Yang, Beijing (CN); Matthew John Ross McGrath, New York, NY (US); Michael Ng, Kowloon (HK); Andrew J. Gano, Louisville, CO (US); Rhea Marie May, Golden, CO (US)

(73) Assignee: Covidien AG (CH)

( * ) Notice: Subject to any disclaimer, the term of this patent is extended or adjusted under 35 U.S.C. 154(b) by 763 days.

This patent is subject to a terminal disclaimer.

(21) Appl. No.: 17/074,093

(22) Filed: Oct. 19, 2020

(65) Prior Publication Data

US 2021/0030265 A1 Feb. 4, 2021

Related U.S. Application Data

(62) Division of application No. 16/188,749, filed on Nov. 13, 2018, now Pat. No. 10,835,115.

(Continued)

(51) Int. Cl.
*A61B 1/267* (2006.01)
*A61B 1/00* (2006.01)
(Continued)

(52) U.S. Cl.
CPC .......... *A61B 1/267* (2013.01); *A61B 1/00042* (2022.02); *A61B 1/00048* (2013.01);
(Continued)

(58) Field of Classification Search
CPC ........ A61B 1/267; A61B 1/0005; A61B 1/053
See application file for complete search history.

(56) References Cited

U.S. PATENT DOCUMENTS 8,194,122 B2    6/2012  Amling et al.
8,652,033 B2    2/2014  Berci et al.
(Continued)

FOREIGN PATENT DOCUMENTS

EP    2433553 A1    3/2012
JP    2005052635 A   3/2005
(Continued)

OTHER PUBLICATIONS

Translation of JP2014210085A.*
(Continued)

*Primary Examiner* — Ellen C Hammond

(57) ABSTRACT

A multifunctional visualization instrument is provided that, in certain embodiments, includes a body having a proximal end and a distal end. The multifunctional visualization instrument includes a display screen on the body and a camera stick at the distal end of the body and comprising an arm and a camera. The arm of the camera stick is sized to fit within a channel of a removable laryngoscope blade. The multifunctional visualization instrument includes a port on a surface of the laryngoscope, configured to mate with an introducer and a steering input for steering the introducer, displayed on the display screen simultaneously with an image of the patient captured by the camera.

20 Claims, 34 Drawing Sheets

Related U.S. Application Data

(60) Provisional application No. 62/674,728, filed on May 22, 2018, provisional application No. 62/636,534, filed on Feb. 28, 2018, provisional application No. 62/586,231, filed on Nov. 15, 2017.

(51) Int. Cl.
*A61B 1/005* (2006.01)
*A61B 1/012* (2006.01)
*A61B 1/045* (2006.01)
*A61B 1/05* (2006.01)

(52) U.S. Cl.
CPC ........ *A61B 1/0005* (2013.01); *A61B 1/00052* (2013.01); *A61B 1/00066* (2013.01); *A61B 1/00105* (2013.01); *A61B 1/00112* (2013.01); *A61B 1/00121* (2013.01); *A61B 1/00124* (2013.01); *A61B 1/00133* (2013.01); *A61B 1/0016* (2013.01); *A61B 1/0051* (2013.01); *A61B 1/0125* (2013.01); *A61B 1/045* (2013.01); *A61B 1/053* (2013.01)

(56) References Cited

U.S. PATENT DOCUMENTS

| | | | |
|---|---|---|---|
| 8,715,172 B1* | 5/2014 | Girgis | A61B 1/05 600/188 |
| 8,746,239 B2 | 6/2014 | Yoshida | |
| 8,827,899 B2 | 9/2014 | Farr et al. | |
| 8,982,199 B2 | 3/2015 | Amling et al. | |
| 9,498,112 B1* | 11/2016 | Stewart | A61B 1/05 |
| 9,538,908 B2 | 1/2017 | Allyn et al. | |
| 9,687,141 B2 | 6/2017 | McGrath | |
| 9,820,641 B2 | 11/2017 | McGrath | |
| 10,149,957 B2 | 12/2018 | Runnels | |
| 2007/0173697 A1 | 7/2007 | Dutcher | |
| 2008/0177146 A1 | 7/2008 | Chen | |
| 2008/0177148 A1 | 7/2008 | Chen et al. | |
| 2008/0312507 A1 | 12/2008 | Kim | |
| 2009/0192350 A1 | 7/2009 | Mejia | |
| 2011/0130632 A1 | 6/2011 | McGrail et al. | |
| 2011/0137127 A1 | 6/2011 | Schwartz | |
| 2014/0160261 A1 | 6/2014 | Miller et al. | |
| 2015/0099935 A1 | 4/2015 | Runnels | |
| 2016/0279365 A1 | 9/2016 | Esnouf | |
| 2017/0105614 A1* | 4/2017 | McWilliam | A61B 1/267 |
| 2019/0133430 A1 | 5/2019 | Inglis et al. | |
| 2020/0254204 A1 | 8/2020 | Moffat et al. | |

FOREIGN PATENT DOCUMENTS

| | | |
|---|---|---|
| JP | 2013235114 | 11/2013 |
| JP | 2014210085 A | 11/2014 |
| WO | 2014184507 A1 | 11/2014 |
| WO | 2022/133248 A1 | 6/2022 |
| WO | 2022/266500 A1 | 12/2022 |

OTHER PUBLICATIONS

EP Search Report for EP Application No. 22204423.2 mailed Jan. 12, 2023 (8 pages).
Chinese Office Action for CN Application No. 201880074025.2 dated Jan. 28, 2023 (11 pages).
Ambu_aScope_3_Large_Brochure_4963605 (Oct. 2017).
Lee, Hyung-Chul, "Real-time endoscopic image orientation correction system using an accelerometer and gyrosensor," PLOS ONE | https://doi.org/10.1371/journal.pone.0186691 (Nov. 3, 2017).
International Search Report and Written Opinion for PCT Application PCT/GB2018/053300 dated Feb. 20, 2019; 15 pgs.
Rothfield, Kenneth; "The video laryngoscopy market: Past, present, and future," Anesthesiology News Guide to Airway Management, 2014, pp. 29-34.
Siena, Francesco Luke, et al.; "The development of a novel steerable bougie to assist in airway management," Austrasian Medical Journal, 2016, vol. 9, No. 5, pp. 124-137. http://dx.doi.org/10.4066/AMJ.2016.2619.
Sowers, Nicholas, et al.; "Use of a flexible intubating scope in combination with a channeled video laryngoscope for managing a difficult airway in the emergency department," The Journal of Emergency Medicine, 2016, vol. 52, No. 2, pp. 315-319.http://dx.doi.org/10.1016/j.jermermed.2015.10.010.
Weissbrod, Philip A., et al.; "Reducing injury during video-assisted endotracheal intubation: The "smart stylet" concept," The Laryngoscope, Nov. 2011, vol. 121, pp. 2391-2393.
Australian Examination Report for AU Application No. 2018366386 mailed Aug. 28, 2023 (5 pages).

* cited by examiner

MULTIFUNCTIONAL VISUALIZATION INSTRUMENT

CROSS-REFERENCE TO RELATED APPLICATIONS

The present application is a divisional application of U.S. application Ser. No. 16/188,749, filed on Nov. 13, 2018, the disclosure of which is incorporated by reference in its entirety for all purposes. U.S. application Ser. No. 16/188,749 claims priority to and the benefit of U.S. Provisional Application No. 62/586,231, filed on Nov. 15, 2017, the disclosure of which is incorporated by reference in its entirety for all purposes. U.S. application Ser. No. 16/188,749 also claims priority to and the benefit of U.S. Provisional Application No. 62/636,534, filed on Feb. 28, 2018, the disclosure of which is incorporated by reference in its entirety for all purposes. U.S. application Ser. No. 16/188,749 also claims priority to and the benefit of U.S. Provisional Application No. 62/674,728, filed on May 22, 2018, the disclosure of which is incorporated by reference in its entirety for all purposes.

BACKGROUND

The present disclosure relates generally to medical devices and, more particularly, to multifunctional visualization instruments that are capable of being used by a single operator and/or as one or both of a laryngoscope or an endoscope.

This section is intended to introduce the reader to various aspects of art that may be related to the present disclosure, as described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea and into the lungs during mechanical ventilation. Such tracheal tubes may include endotracheal (ET) tubes, tracheotomy tubes, or transtracheal tubes. It may be beneficial to visualize the airway to facilitate intubation of the patient. Laryngoscopes are in common use for the insertion of endotracheal tubes into the tracheas of patients during medical procedures. Laryngoscopes may include a light source and imager to permit visualization of the patient's airway to facilitate intubation. A laryngoscope, when in use, extends only partially into the patient's airway, and the laryngoscope may function to push the patient's tongue aside to permit a clear view into the airway for placement of an ET tube. Rigid laryngoscope blades are typically shaped to allow a user to use one hand to manipulate the patient's anatomy to facilitate placement of instruments such as introducers (for example bougies or stylet-loaded ET tubes), which can be held with the user's other hand.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In one embodiment, a multifunctional laryngoscope is provided. The multifunctional laryngoscope includes a body comprising a proximal end and a distal end; a display screen on the body; a camera stick at the distal end of the body and comprising an arm and a camera, the arm sized to fit within a channel of a removable laryngoscope blade; a port on a surface of the laryngoscope, configured to mate with an introducer; and a steering input for steering the introducer, displayed on the display screen simultaneously with an image of the patient captured by the camera.

In another embodiment, a visualization instrument system is provided. The system includes an introducer comprising an articulating distal end. The system also includes a laryngoscope handle including a body; a display screen mounted to the body; a camera coupled to a distal end of the body; and an attachment hub configured to mate with the introducer to removably couple the introducer to the laryngoscope handle and communicate steering controls between the laryngoscope handle and the introducer. The system also includes a laryngoscope blade enclosing the camera within a channel of the laryngoscope blade.

In one embodiment, a multifunctional laryngoscope is provided. The multifunctional laryngoscope includes a body having a proximal end and a distal end; a display screen mounted to the body; a camera stick coupled to the distal end of the body and configured to mate with a laryngoscope blade to removably couple the laryngoscope blade to the body such that a camera carried by the camera stick is disposed within a channel of the laryngoscope blade; and a port on a surface of the laryngoscope configured to mate with an introducer to removably couple the introducer to the body, wherein the port comprises an electrical connector that, when coupled to the introducer, provides a drive signal to one or more components of the introducer.

Features in one aspect or embodiment may be applied as features in any other aspect or embodiment, in any appropriate combination. For example, any one of system, laryngoscope or method features may be applied as any one or more other of system, laryngoscope or method features

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
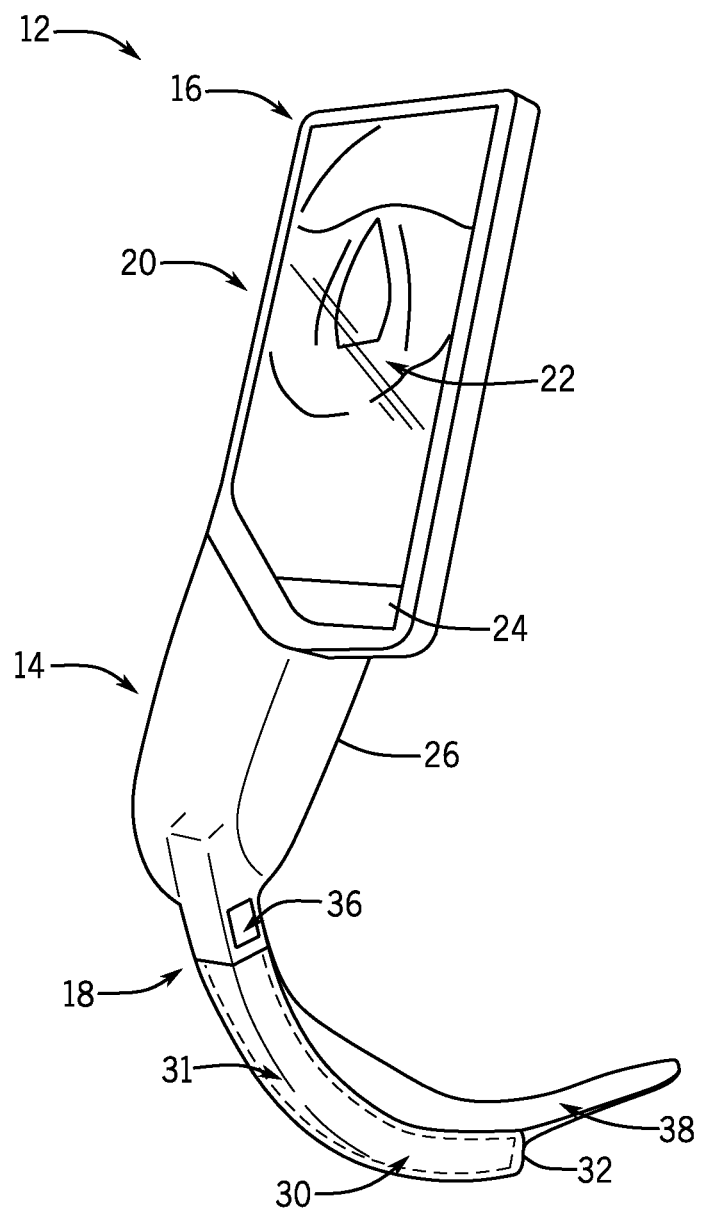
FIG. 1 is a perspective view of a multifunctional laryngoscope, in accordance with certain embodiments of the disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In operation, a caregiver may use a laryngoscope to assist in intubation, e.g., to visualize a patient's airway to guide advancement of the distal tip of an endotracheal tube through the patient's oral cavity, through the vocal cords, into the tracheal passage. Visualization of the patient's anatomy during intubation can help the medical caregiver to avoid damaging or irritating the patient's oral and tracheal tissue, and avoid passing the endotracheal tube into the esophagus instead of the trachea. The caregiver may obtain a direct view of the patient's anatomy by using a laryngoscope to open the patient's mouth and lift the tongue. If the caregiver is using a video laryngoscope which contains a video camera oriented toward the patient, the caregiver may also or alternatively obtain an indirect view of the patient's anatomy by viewing the images captured from the camera and displayed on a display screen. The display screen can be integrated with the laryngoscope, such as mounted on the handle of the laryngoscope, within the caregiver's natural viewing angle looking toward the patient, to enable the caregiver to view the display while manipulating the laryngoscope and endotracheal tube in real time. Accordingly, the user can view the integrated display to guide the endotracheal tube in the airway while also maintaining visual contact with the airway entry to assist in successful intubation.

The laryngoscope may be operated with a single hand (such as the user's left hand) while the other hand (such as the right hand) grips the endotracheal tube and guides it forward into the patient's airway. The user can view advancement of the endotracheal tube on the display screen in order to guide the endotracheal tube into its proper position. The visualization range of the laryngoscope is defined in part by the size of the patient's airway and the position of insertion of a laryngoscope into the upper airway. The user may adjust the viewing angle by manipulating and orienting the laryngoscope within the patient's oral cavity, to account for patient-to-patient variability of anatomy in the airway. In certain implementations, a laryngoscope blade, in which the laryngoscope camera or imaging apparatus is positioned, may extend into the airway from a handle that is gripped and manipulated by the user.

While the video laryngoscope can facilitate more efficient intubation than direct-view intubation, certain patients may benefit from visualization and/or steering devices that extend further into the airway than a laryngoscope. Such visualization may be beneficial for endoscopic placement of endotracheal tubes and/or placement or positioning of suctioning devices in the airway. Endoscope placement (e.g., with an endotracheal tube loaded into the endoscope) may be helpful for anterior or challenging airways. For example, patients with challenging anatomy or limited ability to reposition the head and neck to open the airway a desired degree may benefit from imaging devices that go beyond the visualization range of a laryngoscope and that provide a greater steering range for a camera, or from articulating devices that can be manipulated and moved within the visualization range of the laryngoscope.

An introducer is a thin, flexible instrument (which may be relatively narrower, more flexible, and longer compared to a laryngoscope) that can be inserted into a body cavity for exploration, imaging, biopsy, or other clinical treatments, including catheters, endoscopes (with a camera) or blind bougies (without a camera). Introducers may be positioned to extend into the airway and be steered into the airway passage (such as the pharynx, larynx, trachea, or bronchial tubes) by the user via advancement of the distal end to a desired position and, in certain embodiments, subsequent rotation or repositioning of the introducer. Introducers may be tubular in shape.

An introducer can provide improved access to a patient's airway, but it can be challenging to manage, steer, and manipulate an introducer in conjunction with a laryngoscope and endotracheal tube. The flexibility of the introducer can make it difficult to navigate the distal tip anteriorly (upward, if the patient is lying face-up) through the vocal cords. Additionally, a typical intubating endoscope often requires two hands to operate and, therefore, a single user cannot operate the endoscope while also manipulating a laryngoscope to facilitate endoscope placement. Accordingly, certain techniques involve multiple caregivers separately manipulating the endoscope and the laryngoscope, which is cumbersome and difficult to coordinate. Further, the space around the patient's airway is limited, and the setup for two caregivers, multiple devices (e.g., multiple handles), and multiple displays is bulky and inefficient.

Some endoscopes utilize a remote monitor or medical rack display, but such displays are often outside of the natural viewing range of the user or users performing the intubation. Further, endoscopes are often used in conjunction with a full-sized monitor display that is coupled to the endoscope via a cable and that requires the user to interrupt a working position to view the monitor. Accordingly, the user may not be able to see changes in endoscope camera position or rotation on the display as they are occurring, which may make endoscope steering less efficient. There are difficulties with providing an integrated display screen on a narrow, flexible, or lengthy endoscope that is manipulated, rotated, and steered deep into a body cavity such as an airway.

Provided herein are multifunctional medical devices or multifunctional visualization instruments that, in certain embodiments, may be used as one or both of a laryngoscope or an endoscope and that permit visualization and display of acquired images from both the laryngoscope and the endoscope, either simultaneously or sequentially, on the laryngoscope display. In one embodiment, a multifunctional visualization instrument may operate in a laryngoscope mode, an endoscope mode, or a multifunctional mode that permits simultaneous laryngoscope and endoscope functionality.

Further, the multifunctional visualization instrument may function as a two-piece or two part endoscope. The two-piece endoscope may include a first disposable part that is configured as an elongated flexible introducer (such as in the shape of a wire, cable, catheter, or tube) with a camera at a distal end, and a second reusable part that is configured as a rigid handle and integrated display screen. In this manner, the disposable flexible tube bearing the camera may be removably coupled directly to and controlled by the reusable body that houses power, display, and/or steering control functionality, rather than utilizing a dedicated or integrated gripper or steering mechanism for the endoscope. In this manner, the endoscope introducer many be disposable while the relatively more costly and complex handle and body may be reused.

Further, the multifunctional visualization instrument may be configured as a video laryngoscope that views and controls a blind bougie. In this configuration, a video laryngoscope is inserted into the patient's mouth to obtain an indirect view of the vocal cords, and then a flexible bougie (without a camera) is advanced through the vocal cords, within the view of the video laryngoscope and as shown on the video laryngoscope screen. In an embodiment, the bougie is an articulating bougie and can be actively steered (such as rotated or bent) by the user via controls on the video laryngoscope (such as mechanical buttons on the handle or touch inputs on the display screen). The user can steer the bougie through the vocal cords, then advance an endotracheal tube over the bougie into the desired position, and then remove the bougie and laryngoscope.

The present techniques permit single-user operation of an introducer and a laryngoscope simultaneously for intubation of a patient (or other procedures, as noted in the next paragraph). Further, the present techniques permit visualization of one or both of an endoscope image and laryngoscope image on an integrated laryngoscope display that is positioned on the laryngoscope to permit a natural viewing angle for a user who is looking towards the patient airway. In this manner, the user may simultaneously operate a laryngoscope (to visualize and open the upper airway) while also operating an endoscope or bougie to permit additional access or visualization, such as deeper views of the airway at locations closer to the lungs. A further feature of the multifunctional laryngoscopes is that the user interface features may be configured for one-handed or one finger operation to permit manipulation of the displayed image while steering/advancing the endoscope. In another example, the multifunctional laryngoscope display may be implemented without a menu screen such that the display continuously shows the desired airway image or images without requiring the user to click through settings or options or menus that interrupt the image feed.

While the present techniques are discussed in the context of endotracheal intubation, it should be understood that the disclosed techniques may also be useful in other types of airway management or clinical procedures. For example, the disclosed techniques may be used in conjunction with secretion removal from an airway, bronchial visualization (bronchoscopy), tube exchange, lung biopsy, nasal or nasotracheal intubation, etc. In certain embodiments, the disclosed multifunctional visualization instruments may be used for visualization of anatomy (stomach, esophagus, upper and lower airway, ear-nose-throat, vocal cords), or biopsy of tumors, masses or tissues. The disclosed multifunctional visualization instruments may also be used for or in conjunction with suctioning, drug delivery, ablation, or other treatments of visualized tissue. The disclosed multifunctional visualization instruments may also be used in conjunction with endoscopes, bougies, introducers, scopes, or probes.

The present techniques relate to multifunctional visualization instruments. In certain embodiments, the multifunctional visualization instrument may be implemented as a multifunctional video laryngoscope 12 as shown in FIG. 1. However, it should be understood that certain of the disclosed features of the multifunctional video laryngoscope 12 may be present in or implemented in conjunction with other multifunctional visualization instruments as provided herein. The multifunctional video laryngoscope 12 includes an elongate body 14, which may be ergonomically shaped as a handle to facilitate grip by a user. The body extends from a proximal end 16 to a distal end 18 and includes a display, e.g., a display assembly 20 having a display screen 22. As illustrated, the display assembly 20 is coupled to the proximal end 16 and extends laterally from the body 14 such that a lateral portion 24 of the display assembly 20 extends outwardly away from a sidewall 26 of the body 14. In the illustrated embodiment, the display assembly 20 may be formed as an integrated piece with the body 14, such that a housing of the display assembly 20 and an exterior of the body 14 are formed from the same material. However, in other embodiments, the display assembly 20 may be formed as a separate piece and adhered or otherwise coupled to the body 14. The display assembly 20 may be fixed relative to the body 14 or may be pivotable, such that an angle or the position of the display assembly 22 may be adjusted by the user.

In an embodiment, the laryngoscope 12 also includes a camera stick 30, which may be coupled to the body 14 at the distal end 18 (either fixedly or removably). In certain embodiments, the camera stick 30 may be formed as an elongate extension or arm (e.g., metal, polymeric) housing an image acquisition device (e.g., a camera) and a light source. The camera stick 30 may also house cables or electrical leads that couple the light source and the camera to electrical components in the body 14, such as the display 20, a computer, and a power source. The electrical cables provide power and drive signals to the camera and light source and relay data signals back to processing components in the body. In certain embodiments, these signals may be provided wirelessly in addition to or instead of being provided through electrical cables.

In use to intubate a patient, a removable and at least partially transparent blade 38 is slid over the camera stick 30 like a sleeve. The laryngoscope blade includes an internal channel or passage 31 sized to accommodate the camera stick 30 and to position a camera of the camera stick 30 at a suitable angle to visualize the airway. In the depicted arrangement, the passage 31 terminates at a closed end face 32 positioned such that a field of view of the camera is oriented through the closed end face 32. The laryngoscope blade 38 is at least partially transparent (such as transparent at the closed end face 32, or transparent along the entire blade 38) to permit the camera of the camera stick 30 to capture images through the laryngoscope blade 38. The camera and light source of the camera stick 30 facilitate the visualization of an endotracheal tube or other instrument inserted into the airway.

The laryngoscope 12 may be cleaned and reused for multiple patients. The removable blade 38 protects the components such as the camera stick 30 that would otherwise be exposed to the environment of the upper airway, such as coming into contact with tracheal or oral tissue. The distal end 18 of the body 14 of the laryngoscope 12 may include an attachment feature 36 to facilitate removable or reversible coupling of the laryngoscope blade 38 to the body. For example, the attachment feature 36 may include a protrusion on the body 14, which fits demountably into a recess or passageway formed in a corresponding portion of the laryngoscope blade 38, or vice versa. The laryngoscope blade 38, in certain embodiments, may be configured as a disposable single-use device. Accordingly, in certain embodiments, the multifunctional laryngoscope 12 may be provided as a kit that includes one or more laryngoscope blades 38. The laryngoscope blade 38 may be selected to an appropriate patient size and shape based on an estimate or assessment of the patient's airway, size, or condition, or according to procedure type, or clinician preference.

Figure 2:
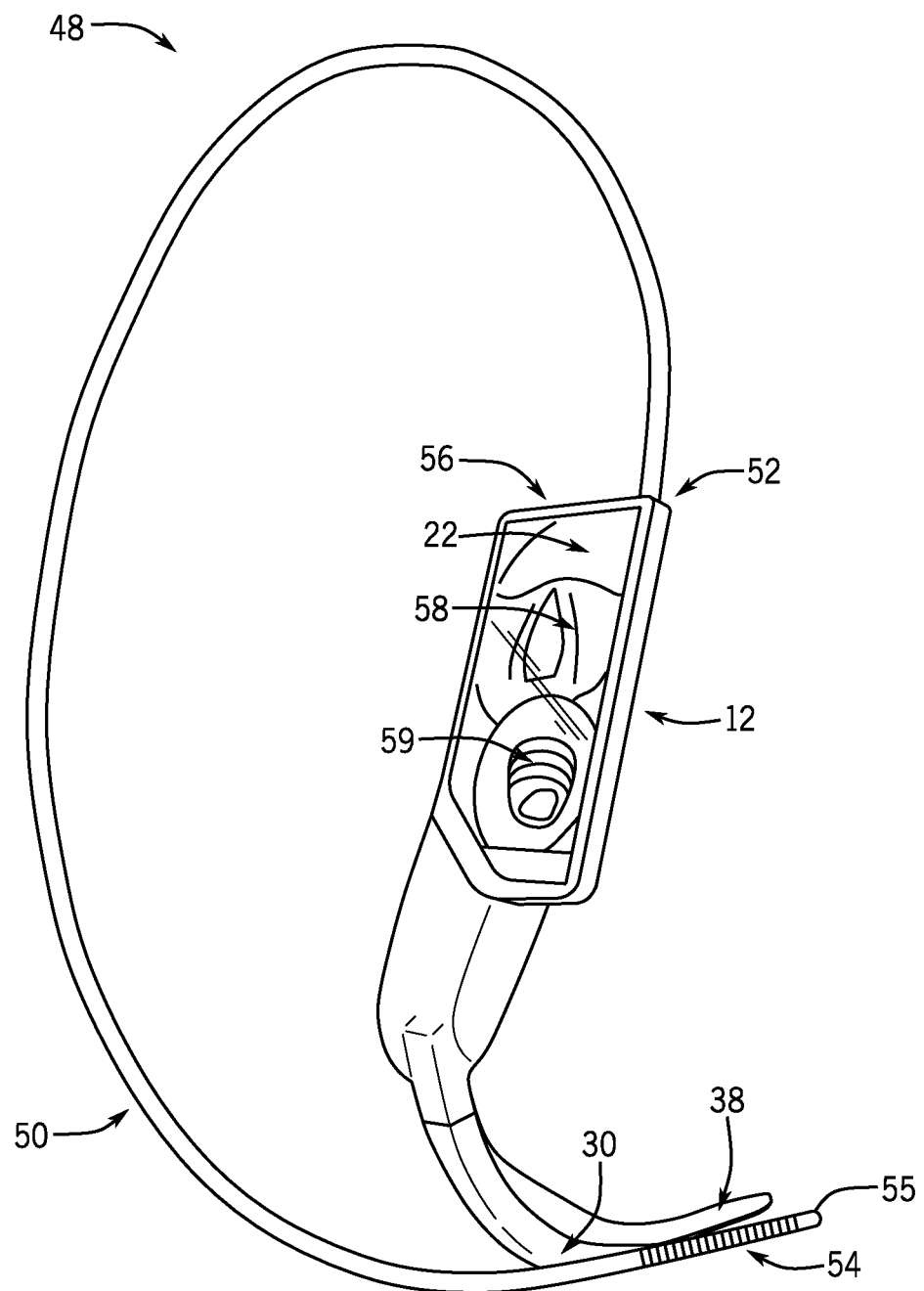
FIG. 2 is a perspective view of a multifunctional laryngoscope coupled to an endoscope, in accordance with certain embodiments of the disclosure.

FIG. 2 is a perspective view of a multifunctional visualization instrument 48, according to an embodiment, that includes a video laryngoscope 12 as provided herein coupled to an introducer 50. The introducer 50 extends from a proximal end 52, which directly couples to the laryngoscope 12, to a free distal end 54. As examples, the introducer 50 may be a steerable blind bougie, with an articulating end 54 that is devoid of any camera or imaging element, or it may be an endoscope with an end 54 which includes an endoscope imaging element, e.g., an endoscope camera 55 (which also may be steerable). In operation, the distal end 54 of the introducer 50 is advanced into the airway. As noted, a user can grip and reposition the laryngoscope 12 with a single hand, and advance the introducer 50 with the other hand. The position of the distal end 54 of the introducer 50 may be controlled via movement of the user's other hand. For example, the user may hold and operate the laryngoscope 12 with the left hand, and use the right hand to advance the distal end 54 towards the lungs or retract the distal end 54 back away from the lungs to reposition the associated bougie or endoscope camera 55. In this manner, the user may operate the multifunctional laryngoscope 12 with one hand and simultaneously advance a coupled introducer with the other hand. However, it should be understood that, in certain implementations, the multifunctional visualization instrument 48 may be held in the right hand while the left hand is used to advance the distal end 54, or the user may switch hands during different operations. In addition, in certain embodiments, the introducer 50 may be advanced into the mouth first, with or without the blade following. In such a scenario (i.e., the handle is being held hovering away from the patient, while the introducer 50 is fed in) the user may hold the handle in either hand. Further, the on-screen controls, e.g., touch controls, button controls, knob controls, may be flipped over, i.e., aligned to the right, so to be reachable with the right thumb in certain embodiments. For example, touch control alignment may be a setup option. Further, button or knob controls may be provided in left-hand or right-hand options depending on the preference of the user.

The display screen 22, as shown, may display the laryngoscope image 58 together with the endoscope image 59 (e.g., the introducer image) when the introducer 50 with a camera 55 is coupled to the laryngoscope body. For example, the display may be a split screen display in which the laryngoscope image 58 is displayed atop the endoscope image 59 or vice versa. In the absence of the coupled introducer 50, the laryngoscope 12 may function in a default operating mode, displaying the laryngoscope image 58 across the full display screen 22. Detection of a coupled introducer 50, e.g., via an electrical coupling or wirelessly, may cause the laryngoscope to operate in a multifunctional mode in which the split screen display is enabled. The dual display permits simultaneous assessment of the status of the upper airway via the laryngoscope camera stick 30 and the lower airway via the endoscope introducer 50. Further, the laryngoscope display screen 22 is positioned on the body 14 at a natural viewing position and permits the user to see real-time effects of movement of both inserted devices within the airway.

Figure 3:
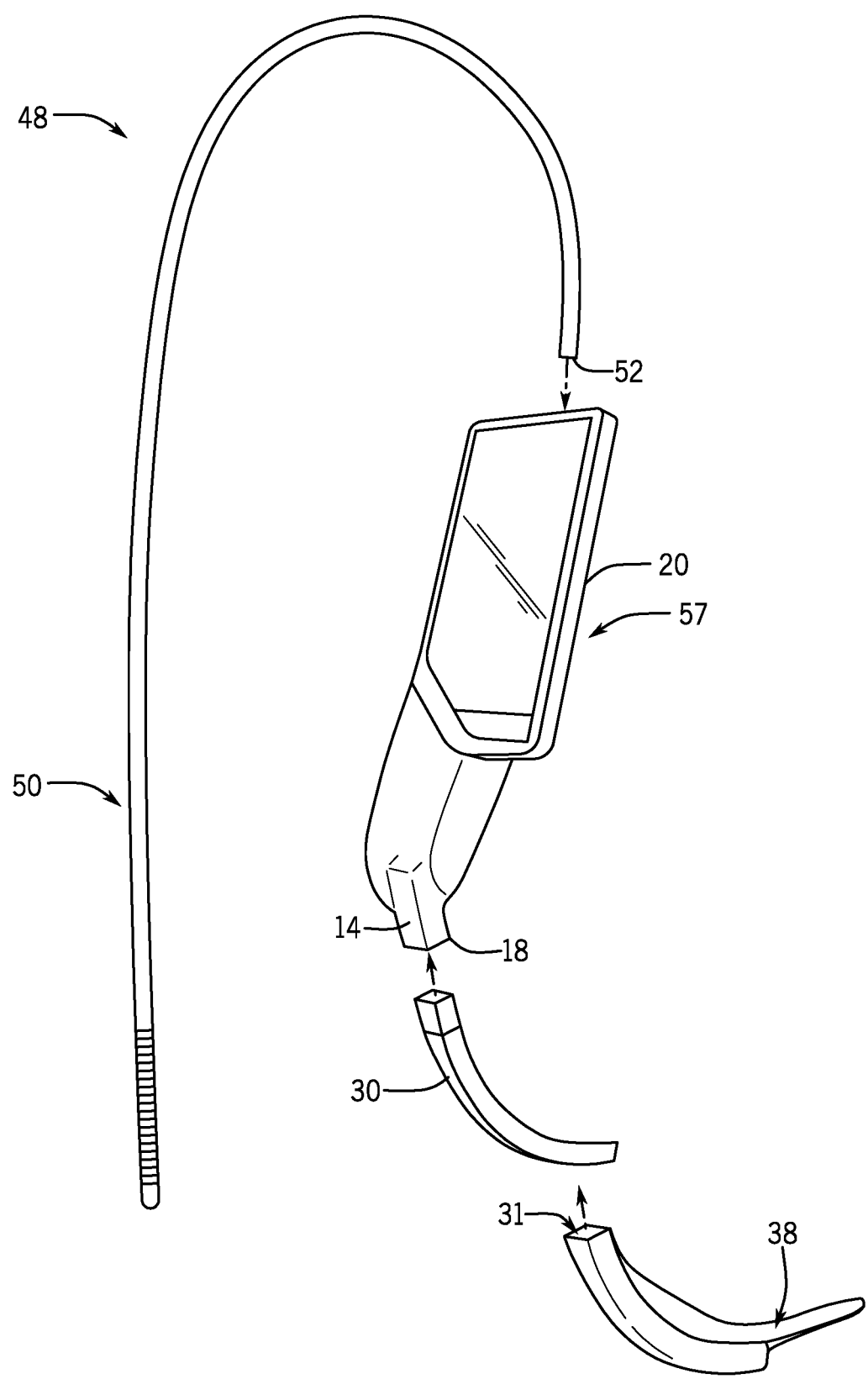
FIG. 3 is a partial perspective view of a multifunctional visualization instrument, in accordance with certain embodiments of the disclosure.

FIG. 3 is a perspective view of an embodiment of a multifunctional visualization instrument 48 in which the body 14 is implemented as a control and display device 57 for one or more removable visualization components. For example, in one embodiment, the control device 57 may be coupled to the endoscope introducer 50 at its proximal end 52 to function as a two-part endoscope to display introducer or endoscope images via the display 20. The distal end 18 of the body may, in certain embodiments, also couple to a removable camera stick 30. The laryngoscope blade 38 may in turn be coupled to the control device 57 via the channel 31 when the camera stick 30 is in place. However, in other embodiments, a camera stick 30 and/or a corresponding connector to receive the camera stick 30 is not present, and the control device 57 does not function as a laryngoscope, but rather as a small, portable, reusable controller for the endoscope introducer 50. In an embodiment, the control device 57 is implemented as a portable, handheld wand, puck, or tablet that is reusable. In an embodiment, the endoscope introducer 50 is a single-use component that is discarded after use, rather than being cleaned or sterilized for use on another patient.

Figure 4:
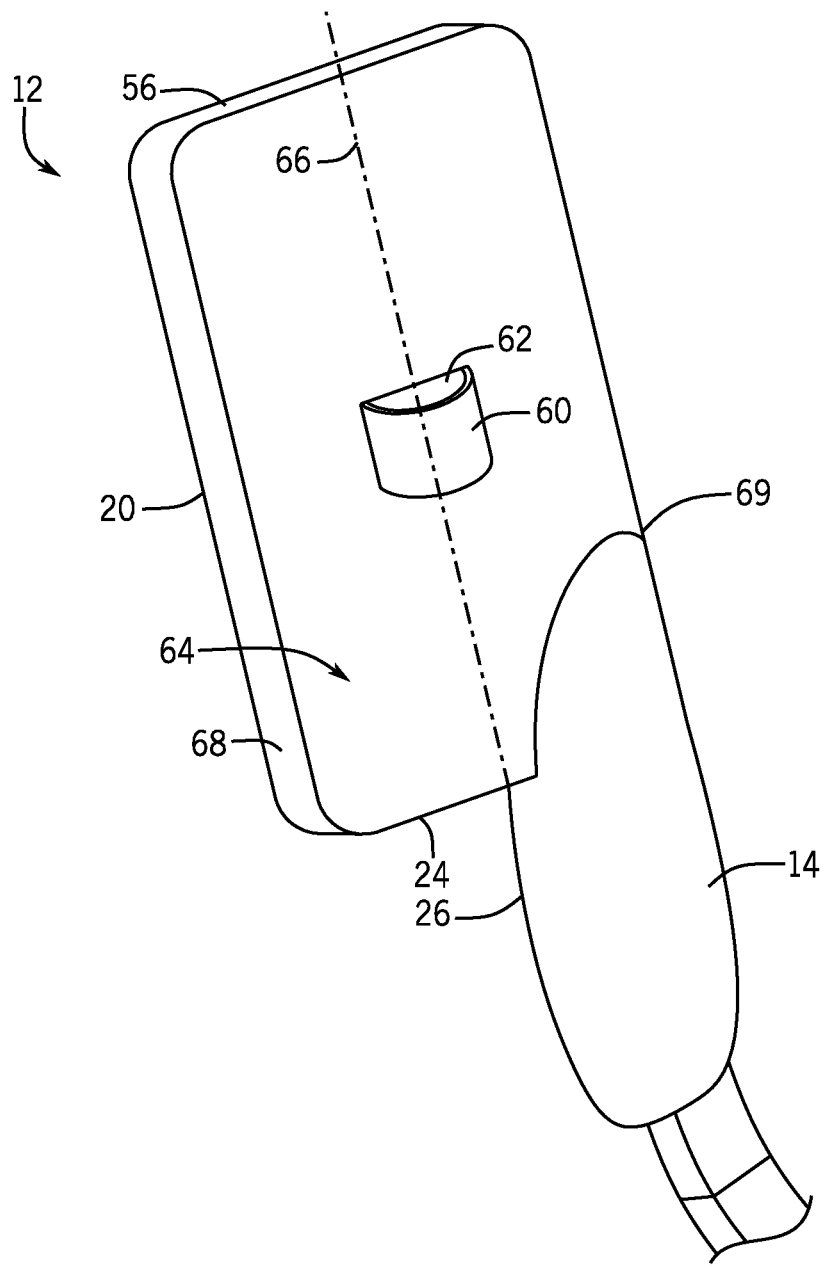
FIG. 4 is a rear partial perspective view of a multifunctional laryngoscope, in accordance with certain embodiments of the disclosure.

In embodiments of the disclosure, the introducer 50 is coupled to a rear of the display assembly 20 and extends over a proximal surface 56 of the display assembly to follow a natural or desired contour of the introducer 50. FIG. 4 is a rear partial perspective view of an embodiment of a multifunctional visualization instrument such as the multifunctional laryngoscope 12. The multifunctional laryngoscope 12 includes an introducer attachment hub 60 (e.g., a port or junction) that forms an opening 62 (or other suitable male or female connector) sized and shaped to connect to the introducer 50 (shown in FIG. 2). The port or hub 60 is located on a rear surface 64 of the display assembly 20 such as along a proximal-distal axis 66 that bisects the display assembly 20 (as shown in FIG. 4). In an embodiment, the endoscope attachment hub 60 may be positioned on the rear surface of the lateral portion 24, such that it is positioned relatively closer to an offset side 68 of the display assembly 22 than an opposing handle side 69 (for example, between the axis 66 and the offset side 68) such that the introducer 50 is offset from the body 14 to prevent the hub 60 and/or the introducer 50 from interfering with the user's grip of the laryngoscope. This offset position can facilitate positioning of the introducer 50 to generally be steered or advanced along the proximal distal direction (e.g., parallel to the bisecting axis 66) while also being offset from the body 14.

Further, the hub 60 may be generally sized and shaped to conform to or mate with a proximal end 52 of the introducer, which in turn is sized to permit an endotracheal tube to be passed over the proximal end 52 and the entire length of the introducer to facilitate intubation or tube switching. In an embodiment, the length of the introducer is tubular in shape. In an embodiment, the introducer has a uniform outer diameter along its entire length (allowing for grooves, markings, or indentations at desired locations), so that passage of an endotracheal tube over the introducer can be smooth and continuous. In an embodiment, this uniform outer diameter includes the proximal end 52 of the introducer, which includes the electrical and/or mechanical connector that mates with the hub 60. Thus, even at the proximal end 52 where the connection to the hub 60 is made, the introducer does not increase in outer diameter. In an embodiment, the outer diameter of the introducer is 5 mm (such that it can pass within an endotracheal tube sized for an adult). In other embodiments, it is smaller or larger.

Figure 5:
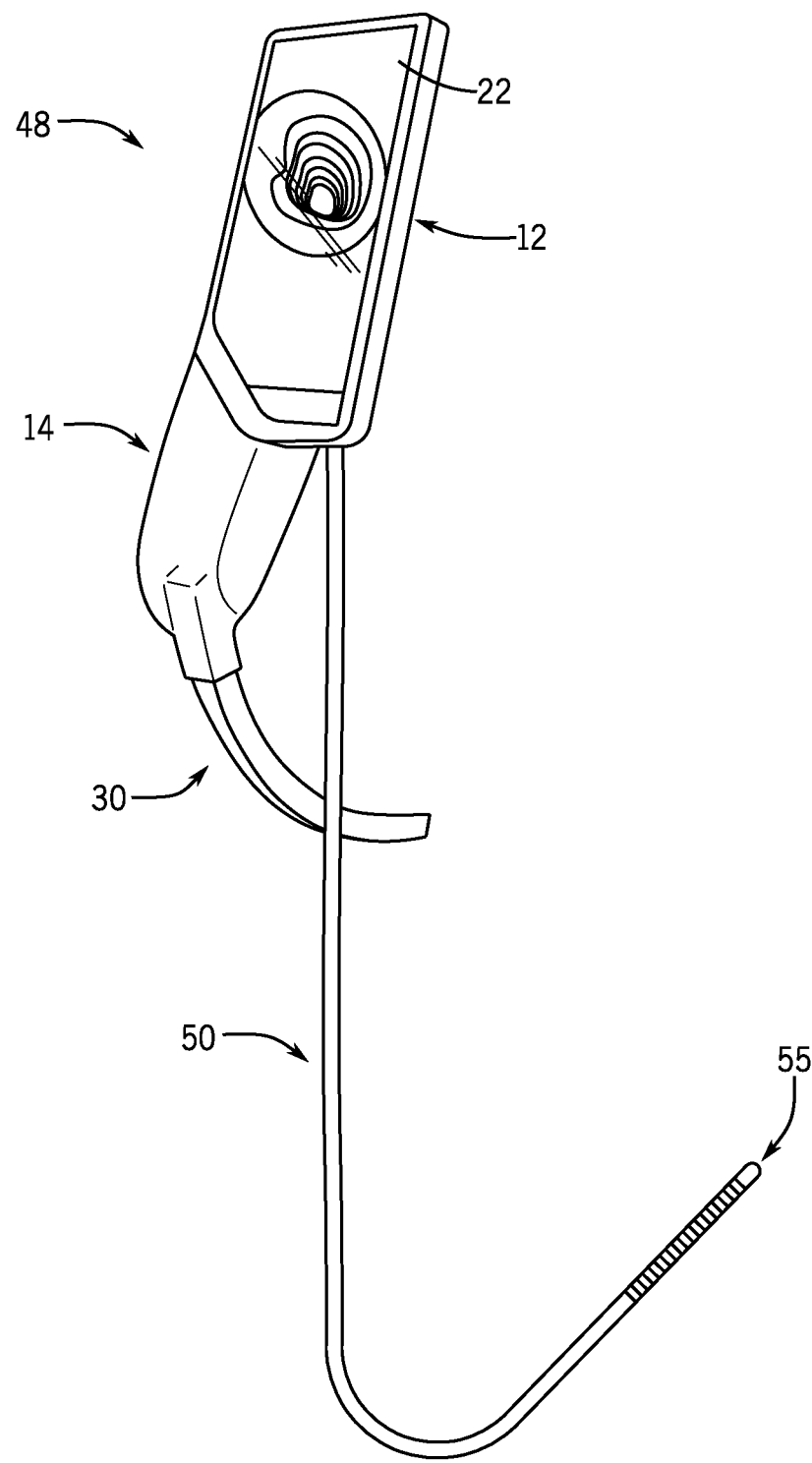
FIG. 5 is a perspective view of a multifunctional laryngoscope coupled to an endoscope and operating to perform endoscopy, in accordance with certain embodiments of the disclosure.

FIG. 5 is an embodiment of the multifunctional visualization instrument 48, in this case the video laryngoscope 12, coupled to the introducer 50, in which the laryngoscope blade 38 (see FIG. 1) is not coupled to the body 14 and the camera stick 30 is not covered or isolated from contact with the patient. Accordingly, in this scenario, the video laryngoscope functionality of the video laryngoscope 12 may not be enabled in the absence of the laryngoscope blade 38 but may be activated upon mounting of a suitable laryngoscope blade 38 to the body 14. However, the multifunctional visualization instrument 48 may retain endoscope functionality even when the video laryngoscope functionality is not enabled or in use. In the depicted embodiment, the absence of the laryngoscope blade 38 when the introducer 50 is coupled may cause activation of an endoscope mode in which the image displayed on the screen is captured from the endoscope camera 55. During endoscope mode, the image shown on the display screen 22 is an image from the endoscope camera 55, and this image extends to fill the entire display screen, as shown in FIG. 5. An icon or other graphic may also be displayed on the screen, or the displayed image may have a boundary with a particular shape (as described below) to indicate to the user that the image being displayed is from the endoscope, rather than from the camera stick. While the camera stick 30 but not the laryngoscope blade 38 is coupled to the body 14, the endoscope mode may entail only providing power to the introducer 50 and not the camera stick 30. The endoscope mode may be triggered via a user input or based on sensed coupling of the introducer 50 together with a signal from a sensor or electrical contact associated with the body 14, camera stick 30, or the attachment feature 36 indicating the absence of the laryngoscope blade 38.

Figure 6:
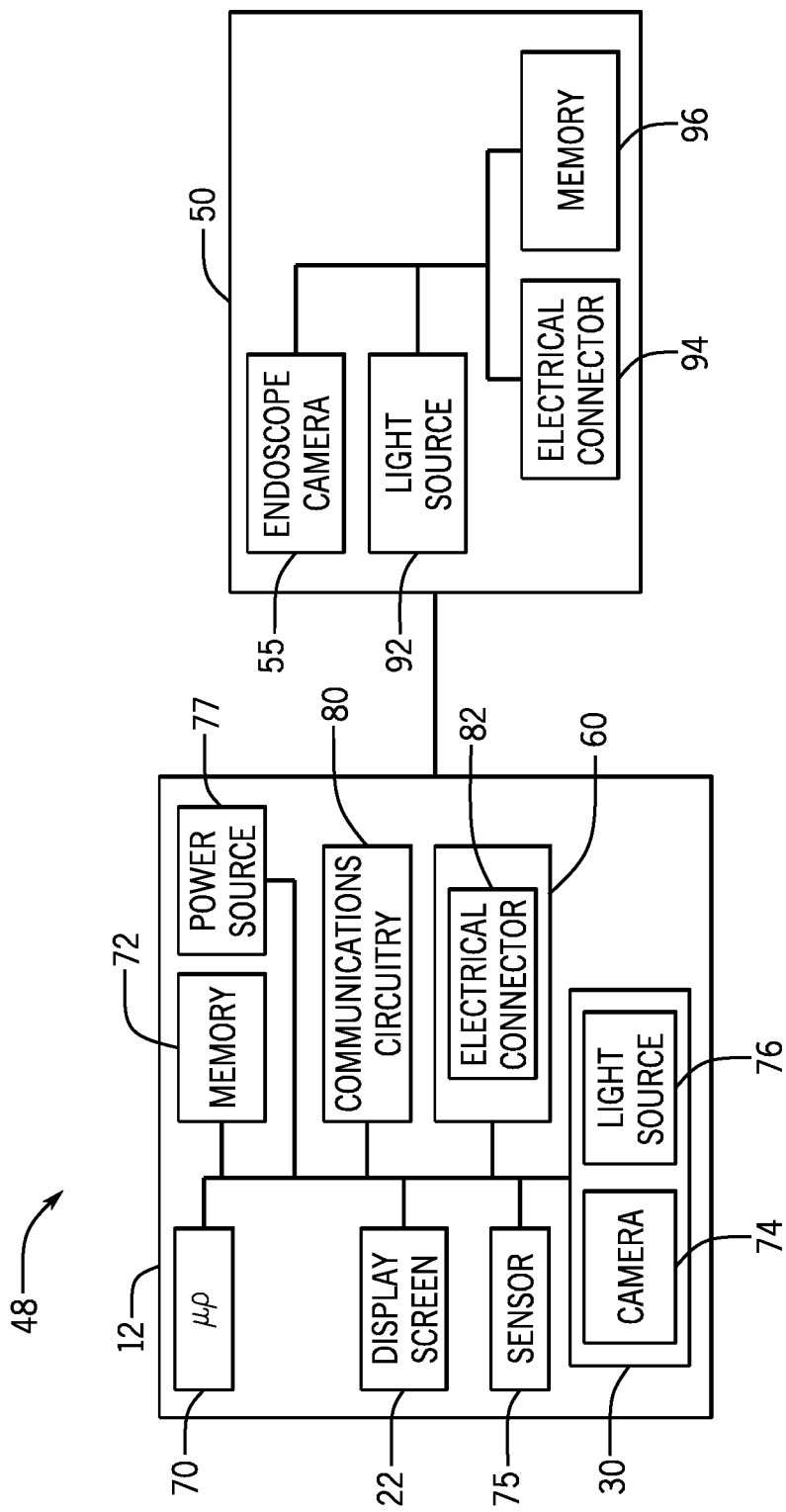
FIG. 6 is a block diagram of the multifunctional laryngoscope system, in accordance with certain embodiments of the disclosure.

When coupled to the multifunctional visualization instrument 48 via the endoscope attachment hub 60, the introducer 50 may function as a plug-and-play device that receives control signals from and sends images to the instrument 48. FIG. 6 illustrates a block diagram of the multifunctional visualization instrument 48, such as a laryngoscope 12. The diagram illustrates the interactions among some of the components of the visualization instrument 48, including the removable introducer 50, the camera stick 30, and the display screen 22. The block diagram also illustrates control circuitry and hardware carried in the visualization instrument 48, including a processor 70, a hardware memory 72, a laryngoscope camera 74 and a laryngoscope light source 76. The processor 70 may execute instructions stored in the memory 72 to send to and receive signals from the laryngoscope camera 74 and to illuminate the light source 76. The received camera signals include video signals (e.g., still images at a sufficiently rapid frame rate to create a video) that are processed and displayed on the display screen 22 of the display assembly 20 (see FIG. 1). The user may provide inputs via a sensor 75 (e.g., a capacitive touch screen sensor on the display screen 22, or mechanical or capacitive buttons or keys on the body 14) to provide user inputs that are provided to the processor 70 to control settings or display characteristics. In certain embodiments, additional user input devices are provided, including one or more switches, toggles, or soft keys.

The visualization instrument 48 may also include a power source 77 (e.g., an integral or removable battery) that provides power to one or more components of the laryngoscope 12. The visualization instrument 48 may also include communications circuitry 80 to facilitate wired or wireless communication with other devices. In one embodiment, the communications circuitry may include a transceiver that facilitates handshake communications with remote medical devices or full-screen monitors. The communications circuitry 80 may provide the received images to additional monitors in real time.

The processor 70 may include one or more application specific integrated circuits (ASICs), one or more general purpose processors, one or more controllers, one or more programmable circuits, or any combination thereof. For example, the processor 70 may also include or refer to control circuitry for the display screen 22 or the laryngoscope camera 74. The memory 72 may include volatile memory, such as random access memory (RAM), and/or non-volatile memory, such as read-only memory (ROM). In one embodiment, the received signal from the laryngoscope camera 74, e.g., image data comprising one or more images, may be processed, enhanced, resized, etc., according to stored instructions executed by the processor 70. Further, the image may be displayed with overlaid indicators or markings. The image data may be stored in the memory 72, and/or may be directly provided to the processor 70. Further, the image data for each patient intubation may be stored and collected for later review. The memory 72 may include stored instructions, code, logic, and/or algorithms that may be read and executed by the processor 70 to perform the techniques disclosed herein.

As mentioned above, the visualization instrument 48 may, in certain embodiments, be coupled to the introducer 50 via the introducer attachment hub 60, which couples the introducer 50 to the visualization instrument 48 via an electrical connector 82 in the hub 60. Once connected, the visualization instrument 48 may receive acquired images from the endoscope camera 55. The power source 77 of the visualization instrument 48 may provide power to the laryngoscope 12 as well as to the coupled introducer 50 and the associated endoscope camera 55 (if present) or other introducer components (such as articulating motors or lights). The visualization instrument 48 may also provide a light drive signal to drive one or both of the laryngoscope light source 76 or an endoscope light source 92 according to instructions provided by the processor 70.

In one embodiment, the processor may detect a signal from an introducer when the introducer is coupled to the hub 60. The signal is passed from the electrical connector 94 of the introducer through the electrical connector 82 of the hub 60, to the processor 70. The signal may be an introducer identification signal that identifies the coupled introducer. For example, the identification signal may be an alphanumeric code, serial number, identification information, or other information stored in a hardware memory 96 on the introducer. Once the signal is detected, the visualization instrument 48 may switch from a default laryngoscope operating mode to a multifunctional visualization instrument operating mode. A similar identification signal may be received from a laryngoscope blade 38. In one embodiment, the memory 72 on the visualization instrument 48 may receive and store laryngoscope blade identification information and/or introducer identification information for an attached laryngoscope blade 38 or introducer 50. The stored information may be retrieved and compared to the introducer identification signal or laryngoscope blade signal to look for a match, for quality or other assessments. The introducer 50 may also include a working channel configured for suctioning (e.g., a suction lumen) or configured to accommodate a device, such as a biopsy tool, an ablation tool, etc. Accordingly, the stored information may also include information about the working channel.

Figure 7:
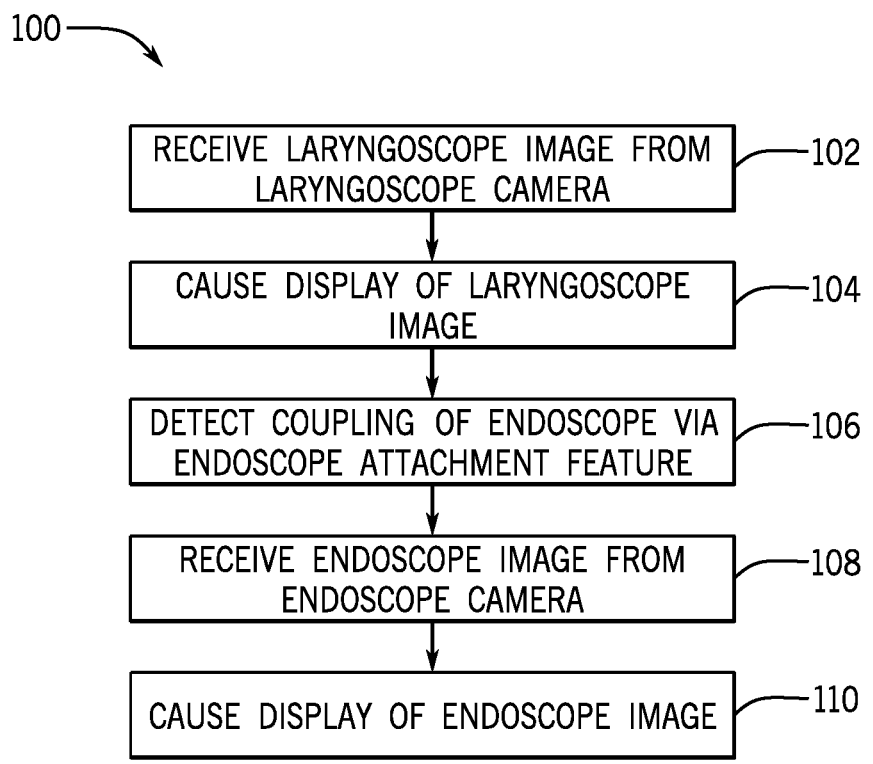
FIG. 7 is a flow diagram for receiving and displaying signals from a laryngoscope imaging device and an endoscope using a multifunctional laryngoscope, in accordance with certain embodiments of the disclosure.

FIG. 7 is a flow diagram illustrating a method 100 for operating a multifunctional visualization instrument, in accordance with an embodiment. One or more of the steps of the method 100 may be executed by the multifunctional laryngoscope 12 coupled to an endoscope introducer 50 (including an endoscope camera 55). The laryngoscope 12, in a default operating configuration, receives images from the laryngoscope camera 74 (block 102). The communication of the laryngoscope images to the processor 70 to cause display of the laryngoscope images at the display screen 22 (block 104) may be facilitated by electrical or wireless connections between the laryngoscope body 14 and the camera stick 30. However, in certain embodiments, the laryngoscope camera 74 may be a wireless device that communicates the laryngoscope images wirelessly, e.g., to the communications circuitry 80.

When the laryngoscope 12 detects coupling of the endoscope via the endoscope attachment hub 60 (block 106), the laryngoscope 12 may operate in a multifunctional operating mode. In this mode, the coupled endoscope introducer 50 acquires endoscope images and relays them to the laryngoscope 12 (block 108). The endoscope images may be received via electrical communication between the endoscope electrical connector 94 and the laryngoscope electrical connector 82. For example, the acquired images may be provided to the processor 70 of the laryngoscope 12 to cause display of the endoscope images at the display screen 22 (block 110). In an embodiment, images from the endoscope camera 55 may be transmitted to the laryngoscope wirelessly, e.g. to the communications circuitry 80. In an embodiment, both the laryngoscope image and the endoscope image are displayed on the display screen simultaneously, such as by switching to a split screen or picture-in-picture mode.

Figure 8:
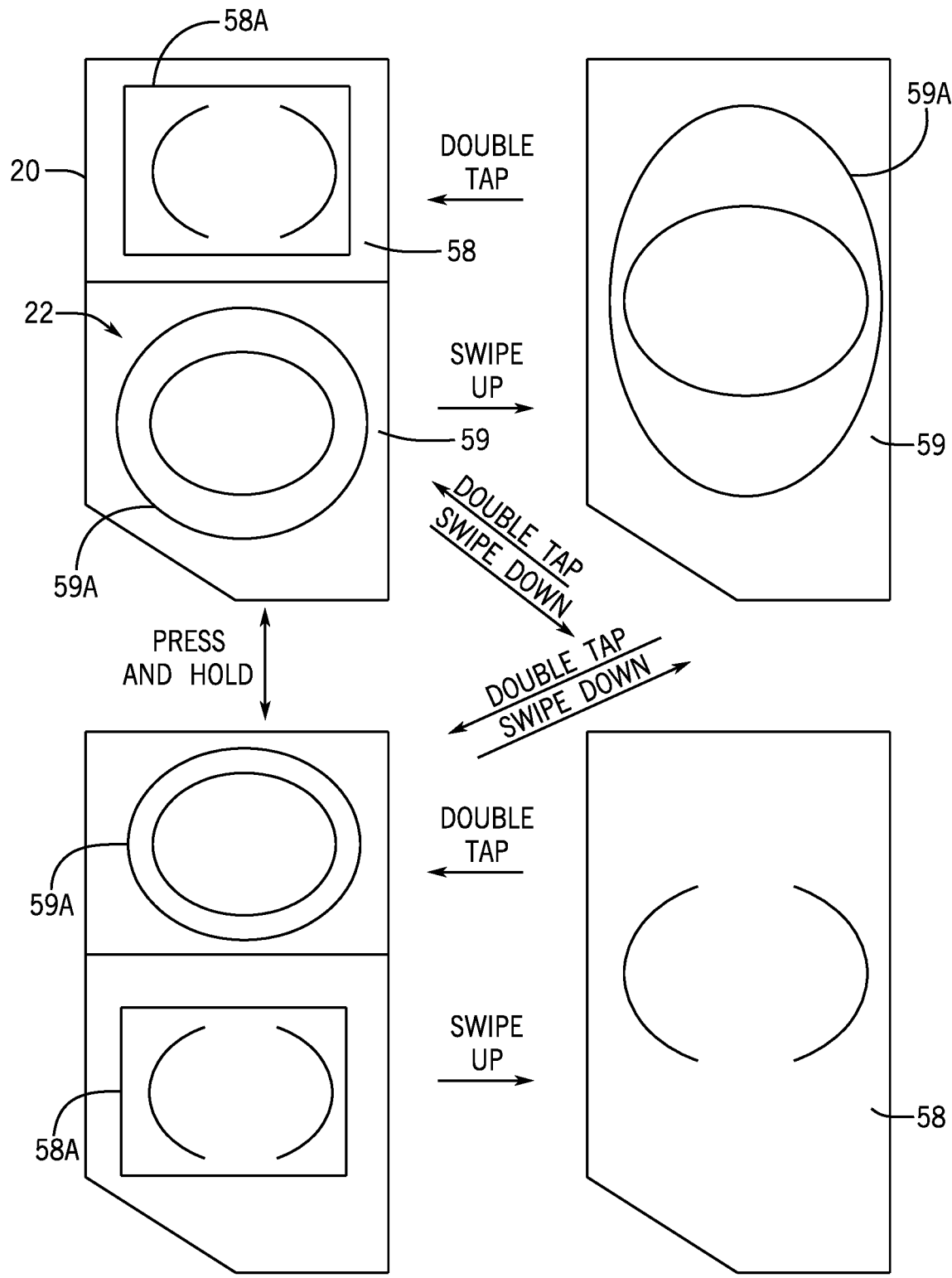
FIG. 8 is a schematic view of examples of different image display configurations of a laryngoscope display, in accordance with certain embodiments of the disclosure.

FIG. 8 shows various display configurations shown on the display screen 22 for the received laryngoscope and endoscope images when the laryngoscope 12 is operating in the multifunctional operating mode. (The hemispheres in image 58 are intended to represent a patient's vocal cords.) It is contemplated that the user may use simple touch motions or inputs to switch between available views. In certain embodiments, the multifunctional operating mode may execute instructions to cause split screen, picture-in-picture, or side-by-side display of the laryngoscope image 58 and the endoscope image 59. The display protocol may default to the split screen display when in the multifunctional instrument operating mode. The depicted embodiments showing user inputs that cause the display 20 to switch between views are by way of example only. In certain embodiments, the user inputs are configured to operate with single finger inputs. For example, as shown in the upper left view of FIG. 8, the split screen display of the laryngoscope image 58 and the endoscope image 59 may be switched to an endoscope image 59 only, shown in the upper right, based on a single finger swipe up (or other input as provided herein) on the display screen 22. In this manner, the two-image display may be switched to a desired single image display using a single finger motion, which permits the user to make such a motion while still being able to grip and generally maintain the position of the multifunctional instrument 48 and/or video laryngoscope 12 while viewing the desired portion of the airway. Further, the relatively simple user inputs limit jostling or manipulation of the patient during intubation. An additional benefit is that images are presented in a direct, continuous, or substantially uninterrupted manner. That is, the switching between images does not involve a menu or settings screen, which would interrupt the user's view of the airway. In an embodiment, while the video laryngoscope 12 is powered on, an image (whether laryngoscope image 58, or endoscope image 59, or both, or switching between various image formats) is displayed uninterrupted on the display screen, and is not covered or obscured by menu screens.

In the depicted example, the switch from single image (either the laryngoscope image 58 or the endoscope image 59) to a two-image display is accomplished via a double tap. The two-image display may be reversed in orientation (reversing which image is above another) by a press and hold motion, and the switch from two-image display to a desired single image is via a swipe up (to select the lower image of a two-image display) or a swipe down (to select the upper image of a two-image display). These transitions are illustrated in FIG. 8. Double tapping on a single image (on the right side of FIG. 8) reverts to the double image display on the top or on the bottom of the left side of FIG. 8, with the most recent single image on the bottom of the double image display (or, alternatively, with the position of the two images based on the layout that was most recently in use by the user). It should be understood that other types of user inputs are contemplated. In one example, because gloves may tend to stick to the display screen 22 during swiping, the user inputs may be swipe-free (such as tapping, double tapping, or pinching), to facilitate ease of use for glove-wearing caregivers.

Certain display settings may be triggered automatically or may be based on default settings. However, the default settings may be overridden based on user inputs as provided herein. For example, the display 20 may switch to a single image view of the laryngoscope image 58 or the endoscope image 59 based on user input that overrides the default display setting. Further, when the introducer 50 is removed or decoupled from the laryngoscope 12 (e.g., via user decoupling of the proximal end 52 from the attachment hub 60), the change or lack of detection of the coupled endoscope may trigger an automatic resumption of the laryngoscope operating mode, resuming display of only the laryngoscope image 58. That is, decoupling of the introducer 50 causes an automatic stop of display of the endoscope image feed and places the laryngoscope image feed on the display screen.

In one embodiment, the laryngoscope image and the endoscope image have different unique shapes or borders, and these shapes or borders are maintained, regardless of the position of the images on the display screen 22. For example, as shown in FIG. 8, the laryngoscope image 58 is maintained in a rectangular or square shaped border 58A and the endoscope image 59 is maintained as an oval or circular shaped border 59A in all four of the display configurations. By maintaining the borders of each image in expected shapes, the user may easily determine which image is on the display screen 22 and in which position. Accordingly, in one embodiment, the laryngoscope image 58 may be displayed within a predefined border having a first shape while the endoscope image 59 may be displayed within a predefined border having a second, different shape. The image border shape may be maintained, regardless of the position of the images on the display screen 22. Further, as the scale of the images changes, the scale of the borders may change in a corresponding manner, to retain the shape. As shown in a lower right panel of FIG. 8, the square or rectangular border of the laryngoscope image 58 may scale proportionally to fill the display screen 22 when the display screen itself is has square or rectangular borders.

Figure 9:
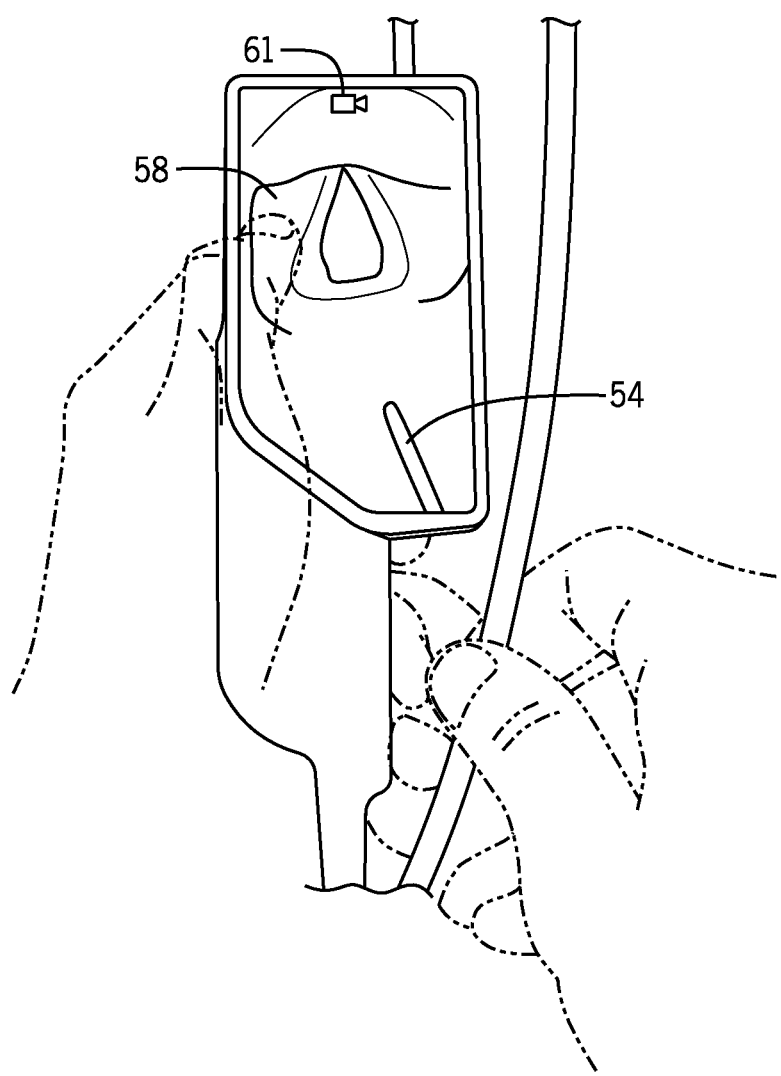
FIG. 9 is a schematic illustration of a multifunctional laryngoscope display, in accordance with certain embodiments of the disclosure.

FIGS. 9-18 show alternative embodiments of display configurations of the laryngoscope image 58 and/or the endoscope image 59. FIG. 9 shows an example of a single image display in which the laryngoscope image 58 fills the screen. The depicted display configuration may be used in conjunction with the video laryngoscope 12 or as a display option with the multifunctional instrument 48. Also shown is a video indicator 61, referring to an active video image mode relative to a still image mode. For example, when recording video, the video indicator 61 will be displayed along with the elapsed recording time. If not recording, the video indicator 61 is not displayed. The video laryngoscope 12 and/or the multifunctional instrument 48 may be capable of recording video or still images based on user inputs. Such inputs may be soft keys or buttons positioned on the body 14 of the video laryngoscope 12 or touch inputs on the display screen.

Figure 10:
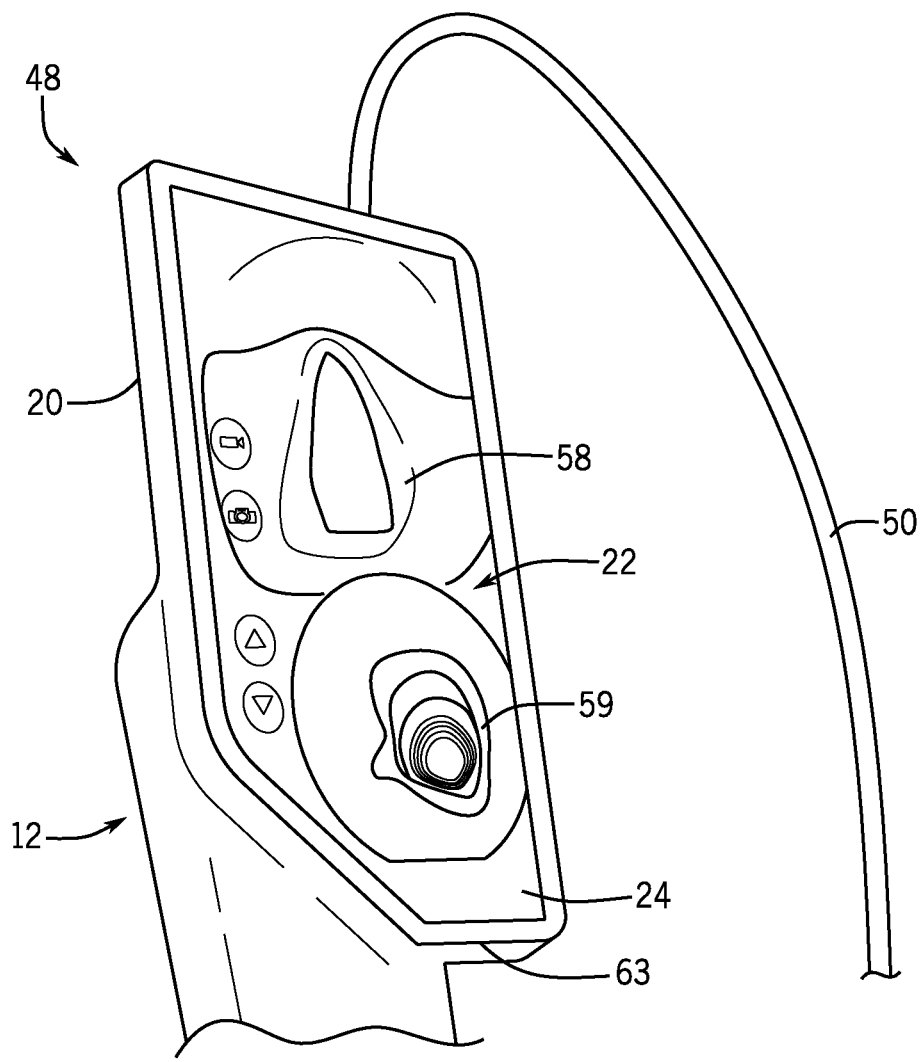
FIG. 10 is a schematic illustration of a multifunctional laryngoscope display, in accordance with certain embodiments of the disclosure.
Figure 11:
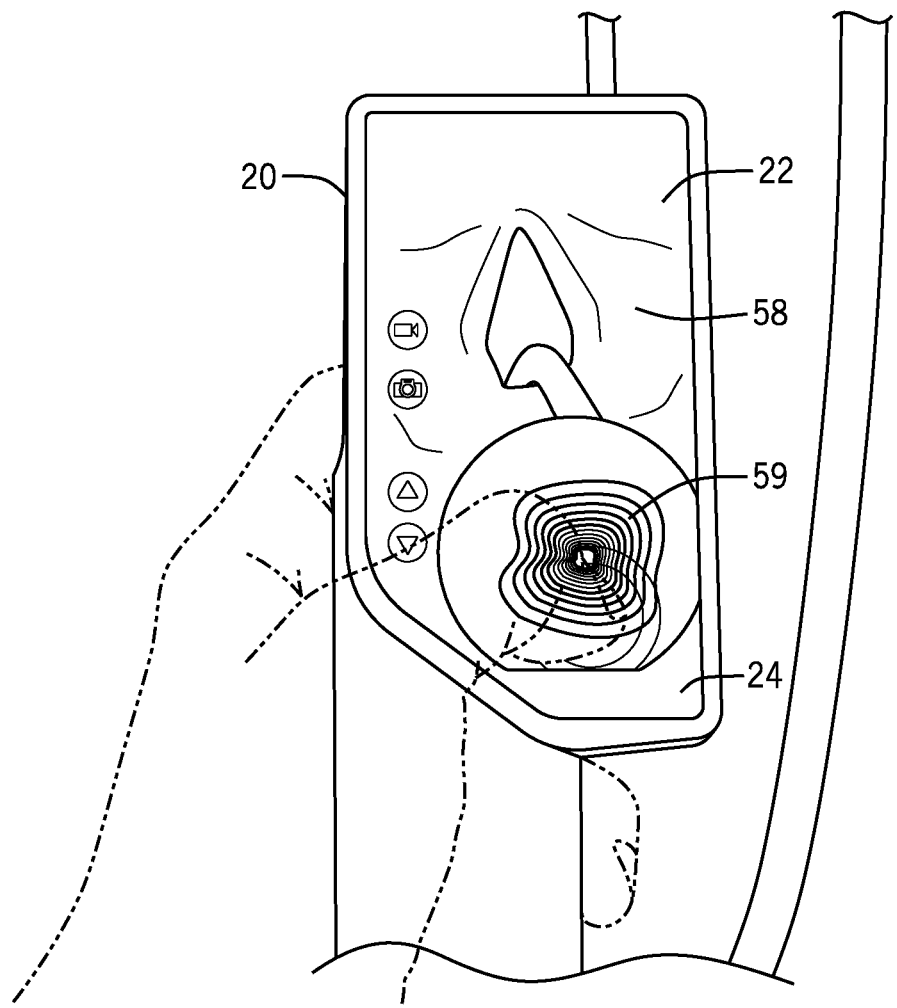
FIG. 11 is a schematic illustration of a multifunctional laryngoscope display, in accordance with certain embodiments of the disclosure.
Figure 12:
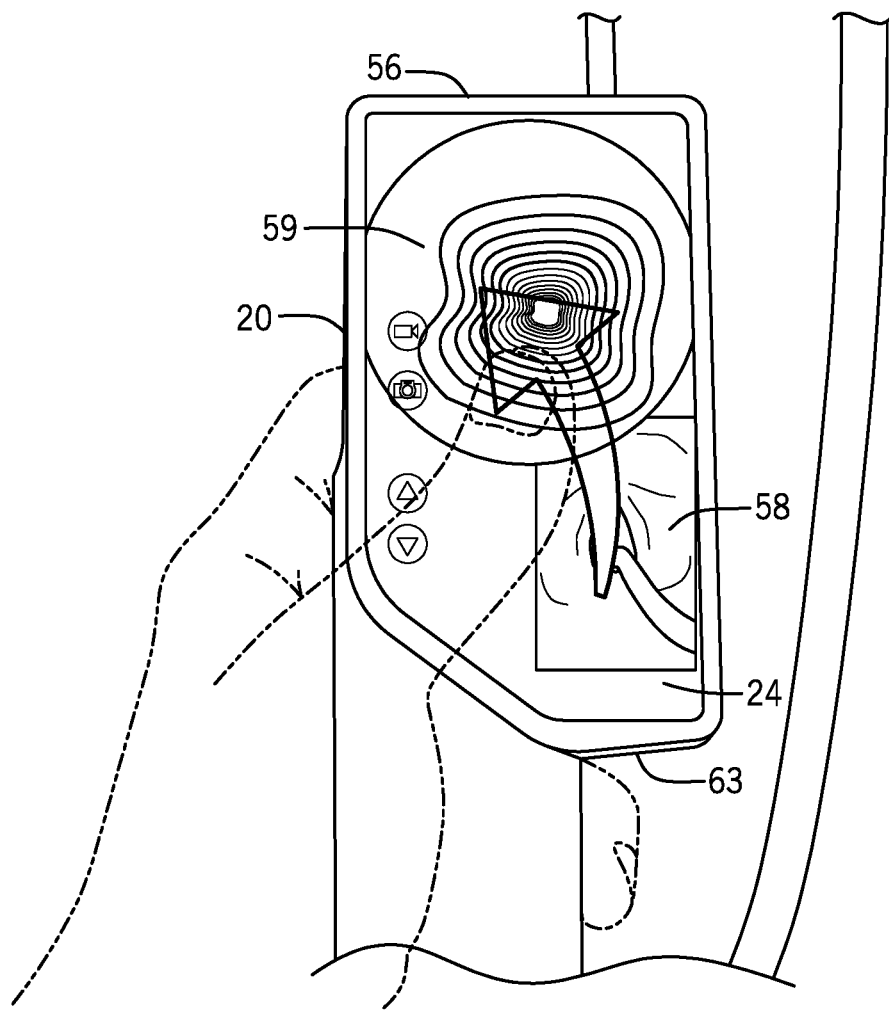
FIG. 12 is a schematic illustration of a multifunctional laryngoscope display, in accordance with certain embodiments of the disclosure.

FIG. 10 shows an example of the picture-in-picture configuration (in which the lower smaller image partially overlaps the larger image) when the video laryngoscope 12 is coupled to the endoscope introducer 50 to operate as the multifunctional instrument 48. In certain embodiments, the displayed configuration is a default setting triggered by coupling of the endoscope introducer 50 to the video laryngoscope 12. The endoscope image 59 is positioned adjacent a distal portion 63 of the display screen 22 or within the lateral portion 24. This setting may be based on empirical preference data for users. However, the default setting may be overridden as provided herein. For example, as shown in FIG. 11, using just a single finger (shown as a thumb in the depicted image), the user may tap (or press and hold, swipe left or right, etc.) to switch to a single image display (e.g., as shown in FIG. 8), or the user may swipe up on the endoscope image 59 (as shown in the progression from FIG. 11 to FIG. 12) to reverse the images, such that the laryngoscope image 58 is the smaller, overlapped image positioned adjacent the distal portion 63 of the display 20 and the endoscope image 59 is the larger, overlapping image closer to the proximal end 56 of the display 20. In an embodiment, one of the two images (either the endoscope image or the laryngoscope image) overlaps the other one, regardless of which image is at the top or bottom of the screen. For example, in FIG. 11 and FIG. 12, the endoscope image overlaps the laryngoscope image in both positions.

Figure 13:
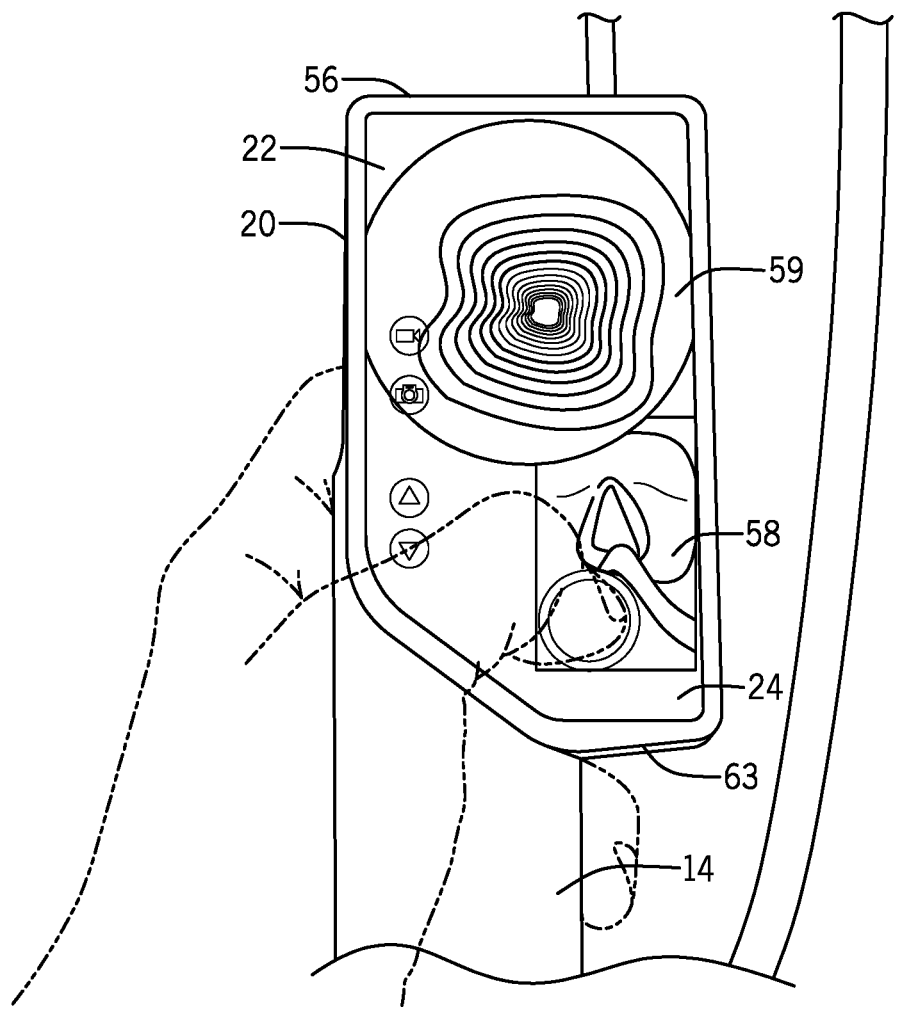
FIG. 13 is a schematic illustration of a multifunctional laryngoscope display, in accordance with certain embodiments of the disclosure.
Figure 14:
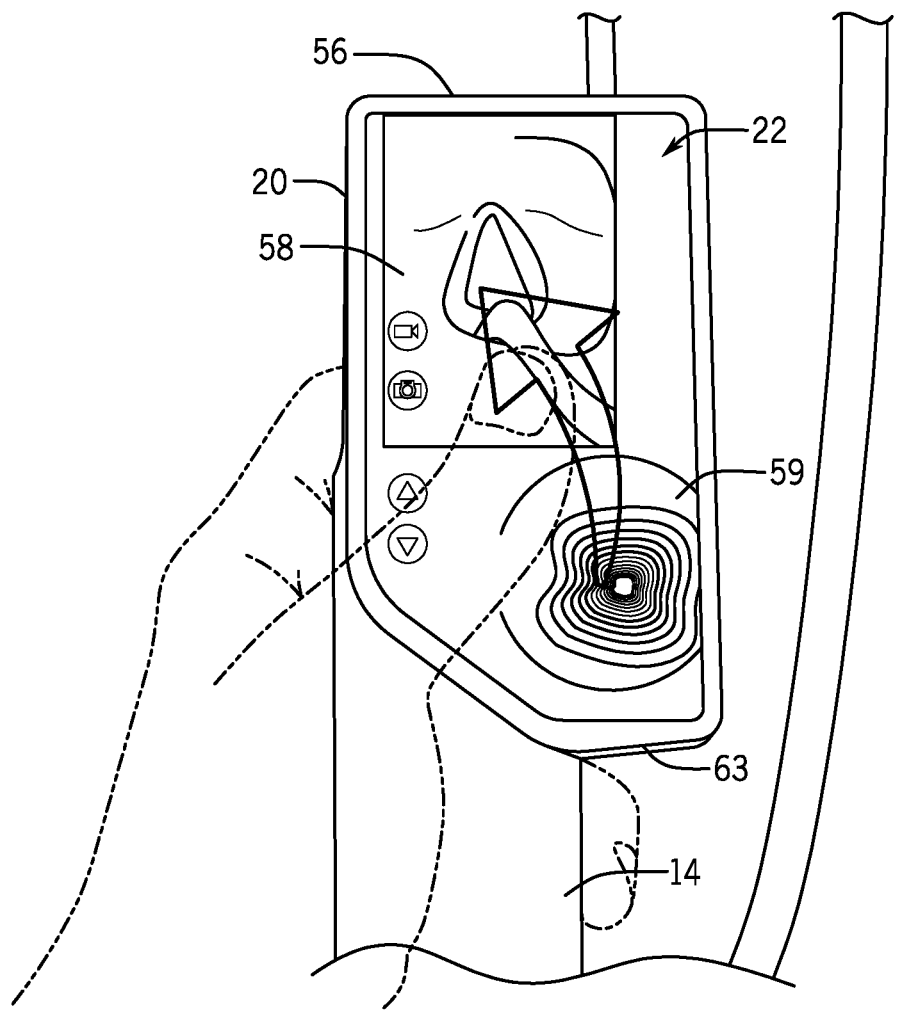
FIG. 14 is a schematic illustration of a multifunctional laryngoscope display, in accordance with certain embodiments of the disclosure.

Similarly, as shown in the progression from FIG. 13 to FIG. 14, the user may swipe on either image (swiping down on the larger, upper endoscope image 59 or, as shown, swiping up on the smaller, lower laryngoscope image 58) to cause the images to reverse position. Additionally, in the either configuration, the user may tap (or press and hold, etc.) on one of the images to return to a single image display of that image.

Figure 15:
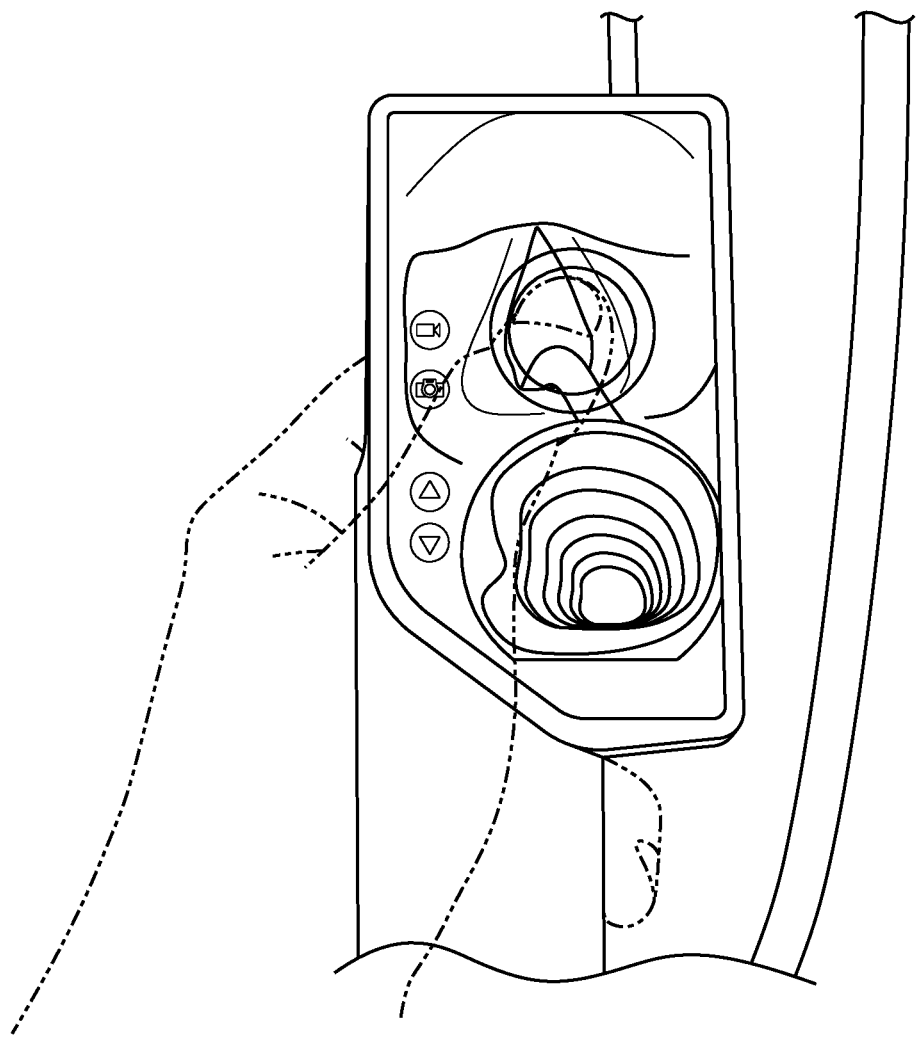
FIG. 15 is a schematic illustration of a multifunctional laryngoscope display, in accordance with certain embodiments of the disclosure.
Figure 16:
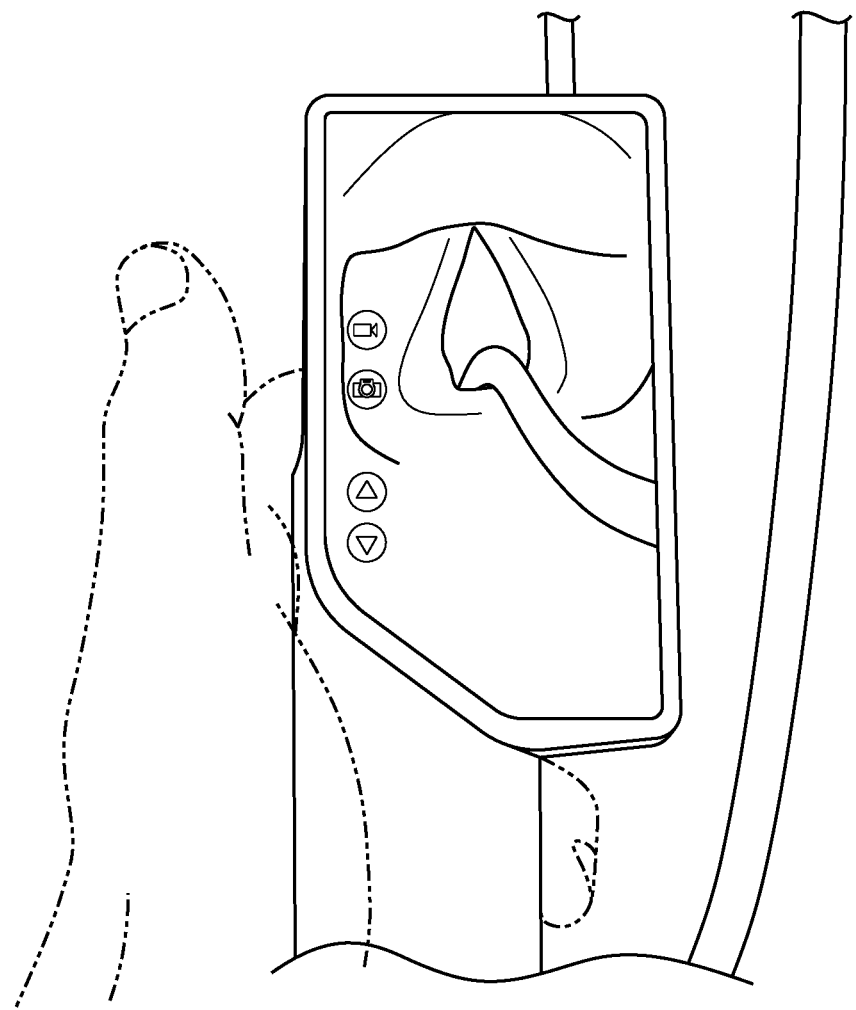
FIG. 16 is a schematic illustration of a multifunctional laryngoscope display, in accordance with certain embodiments of the disclosure.
Figure 17:
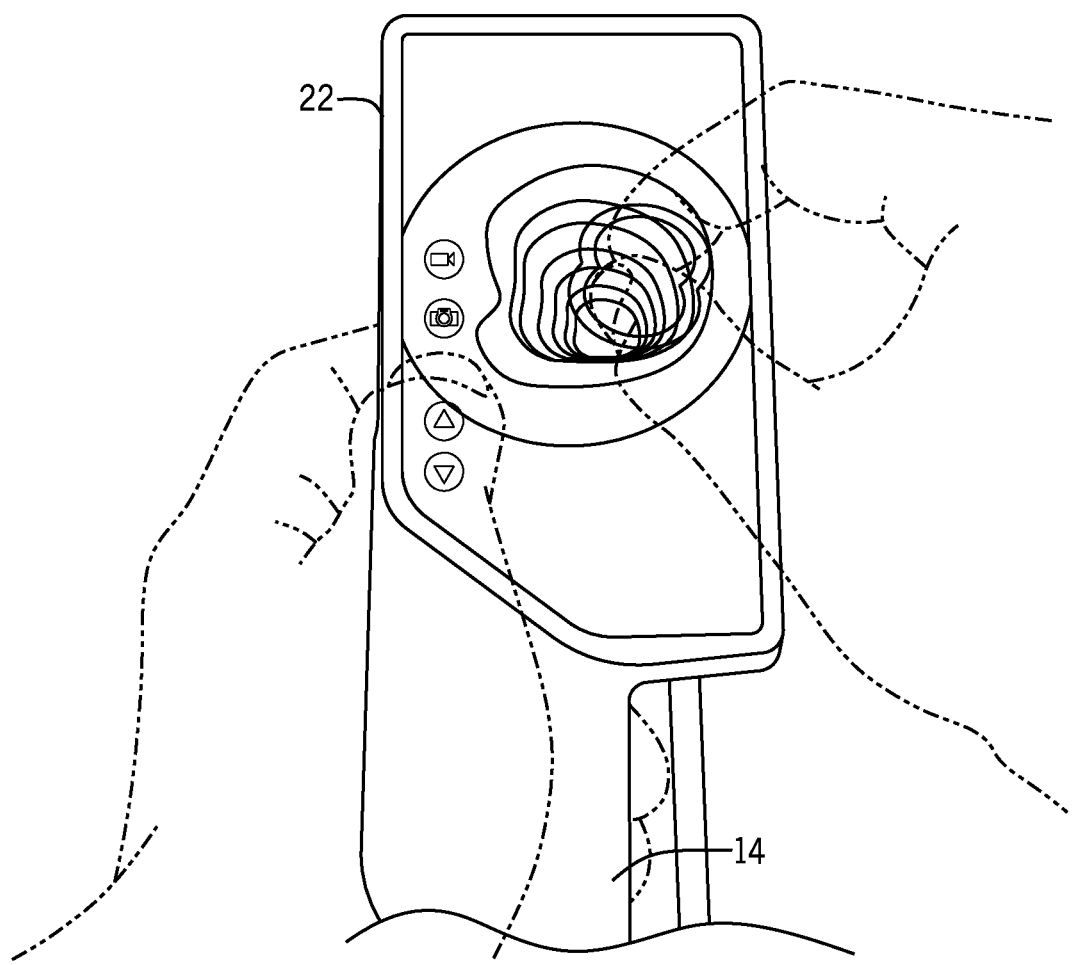
FIG. 17 is a schematic illustration of a multifunctional laryngoscope display, in accordance with certain embodiments of the disclosure.
Figure 18:
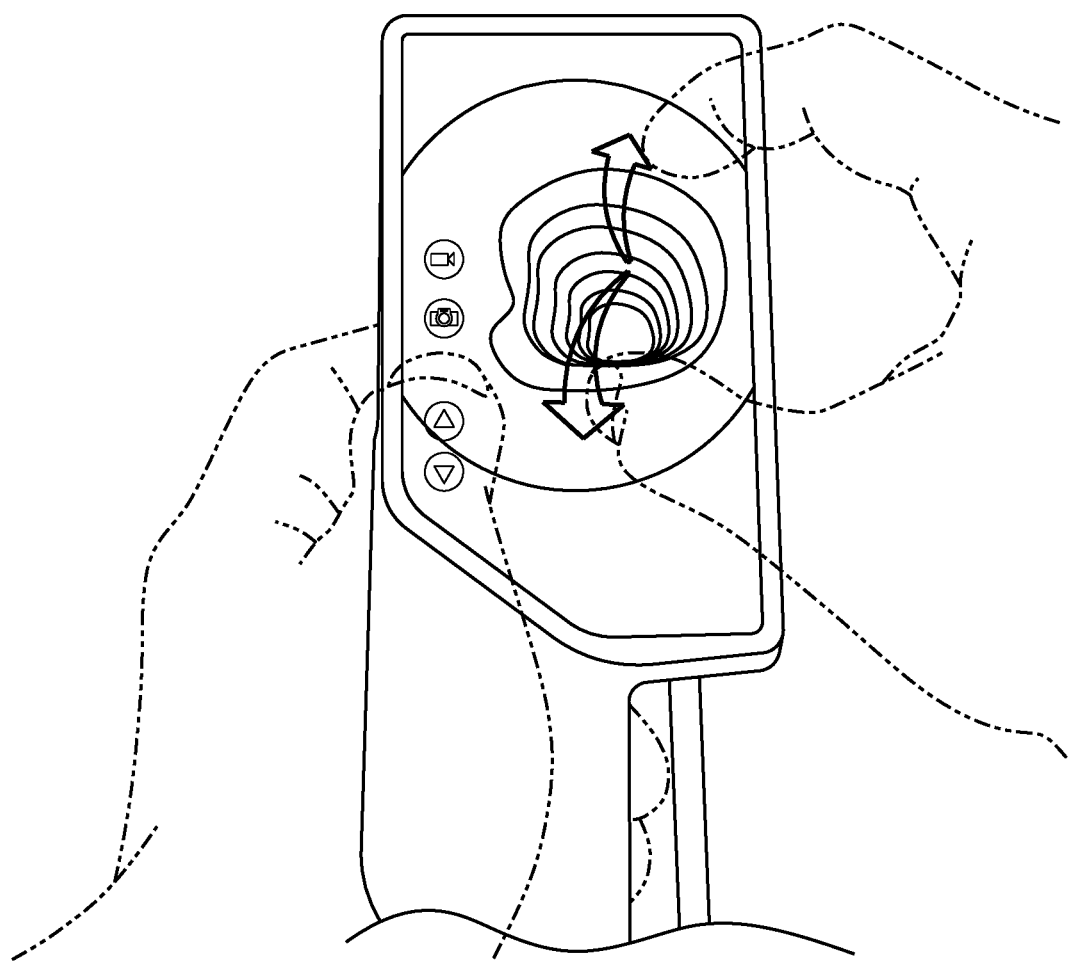
FIG. 18 is a schematic illustration of a multifunctional laryngoscope display, in accordance with certain embodiments of the disclosure.

In certain embodiments, the user input functions may be active (i.e., responsive to user motions) only in the portion of the screen that may generally correspond with areas closer to a user's left thumb while the user is also gripping the body 14, such as in the lower half, lower third, lower two-thirds, or other thumb-reachable portion of the screen 22. However, in other embodiments, the user may provide user inputs anywhere on the display screen 22. For example, FIG. 15 shows a tap and hold or double tap type input on the laryngoscope image 58 to cause display of the laryngoscope image 58 in full screen, resulting in the configuration shown in FIG. 16. Further, while image manipulation may be generally configured for single-finger inputs, certain functions may involve gripping the laryngoscope body with the left hand while using the right hand to pinch (FIG. 17) or spread (FIG. 18) the image on the display screen 22 to zoom in or out. In another embodiment, to promote single-hand operation, gesturing to the right over the view with the thumb may zoom the image in and gesturing to the left may zoom the image out (or vice versa).

Figure 19:
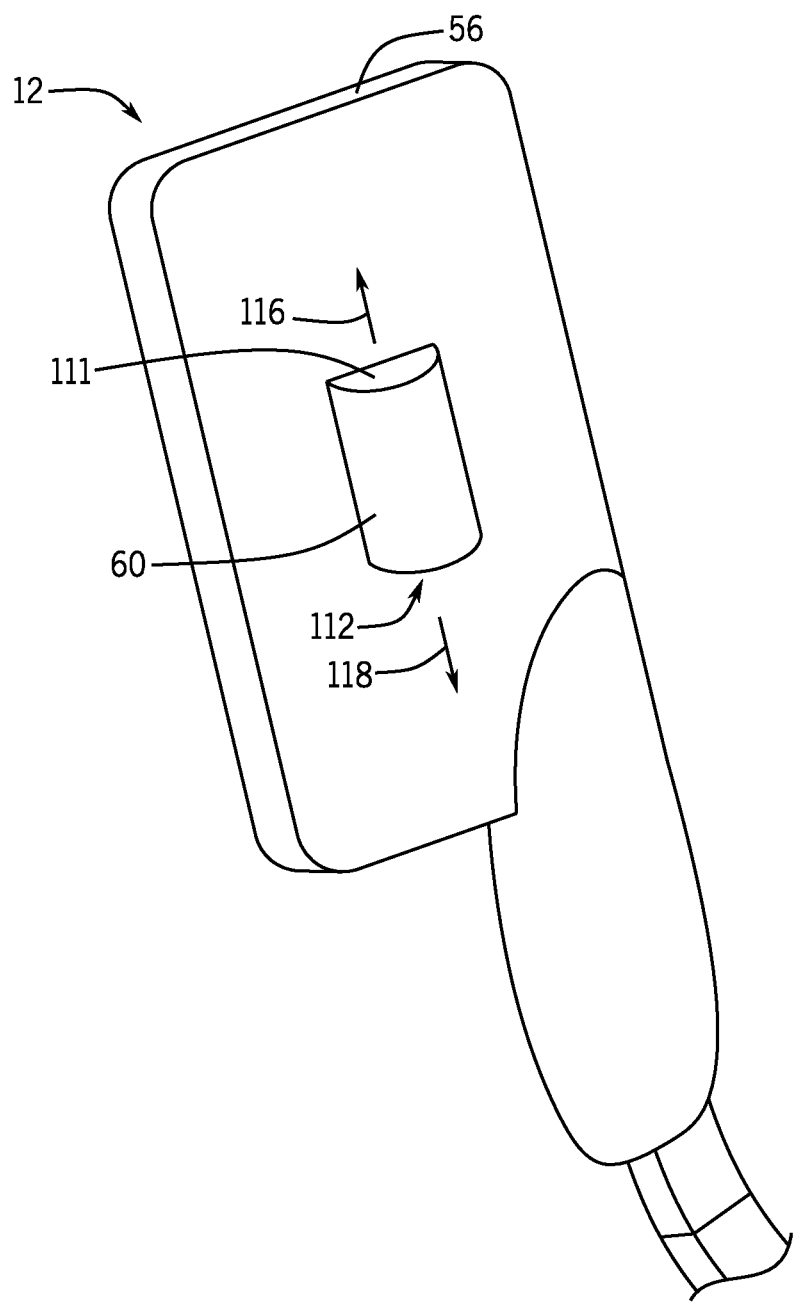
FIG. 19 is a rear perspective view of a bidirectional port or attachment hub of a multifunctional laryngoscope, in accordance with certain embodiments of the disclosure.

FIG. 19 is a partial rear perspective view of the multifunctional laryngoscope 12 showing an example of the introducer attachment hub 60 that permits bi-directional attachment of the introducer 50 (see FIG. 2). The endoscope attachment hub 60 may be configured as a bi-directional port including a first opening 111 (or other male or female connector) facing in a proximal direction and a second opening 112 (or other male or female connector) oriented 180 degrees from the first opening, and facing in a distal direction. These two openings 111 and 112 may connect to each other to form one connected channel or passage through the hub 60. When coupled via the first opening 111, the introducer 50 extends in an upward direction 116 positioned to bend or turn over the proximal surface 56 of the display screen 22. When coupled via the second opening 112, the introducer 50 extends in a downward direction 118 that is oriented in a generally distal direction. The endoscope attachment hub 60 may be configured to detect if the introducer 50 is coupled via the first opening 111 or the second opening 112 and automatically trigger the appropriate display protocol. For example, coupling the introducer via the second opening 112 may be associated with a tube exchange protocol. Each of these different orientations may be useful for particular medical procedures, and examples are given below.

Figure 20:
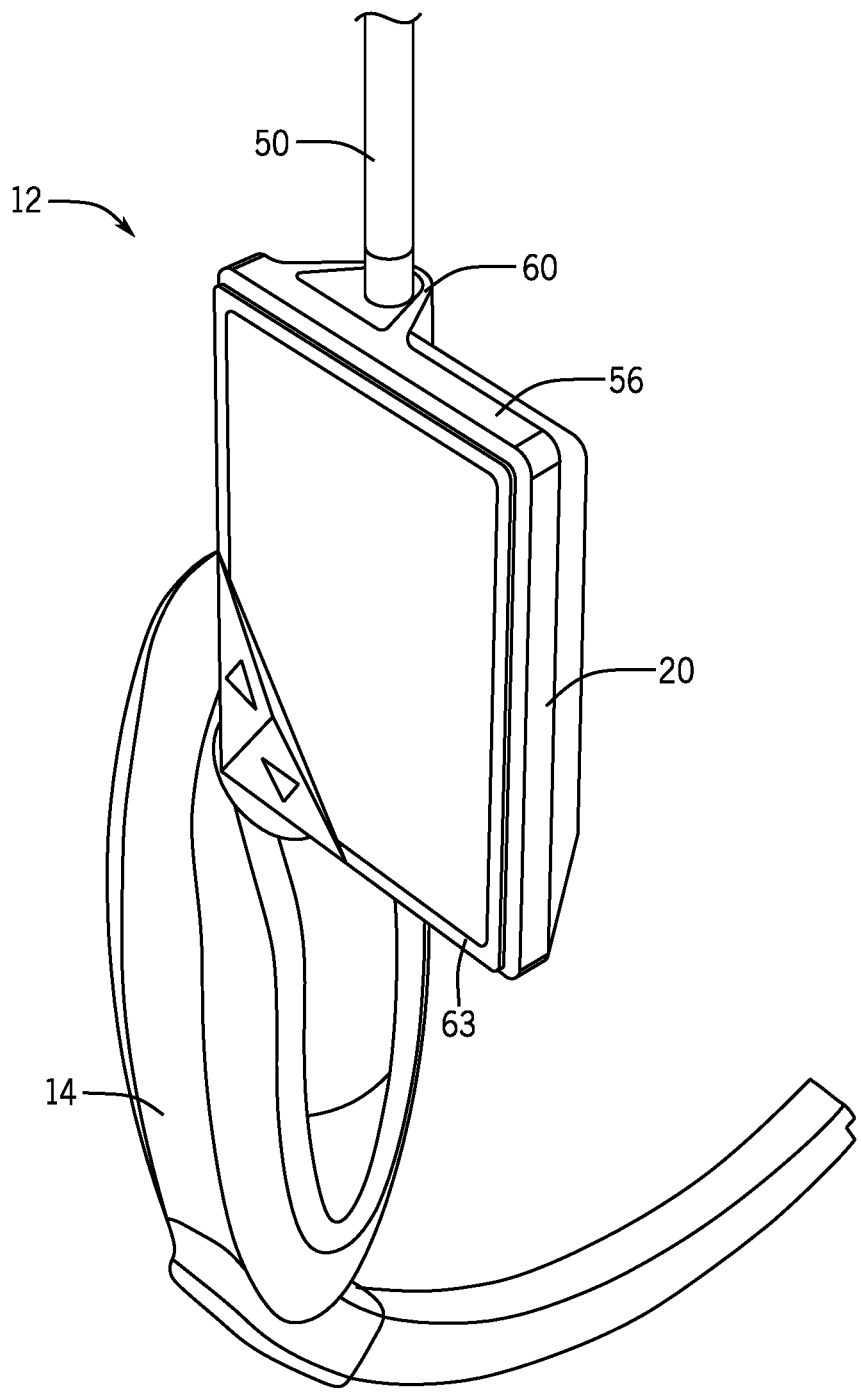
FIG. 20 is a partial perspective view of a multifunctional laryngoscope, in accordance with certain embodiments of the disclosure.
Figure 21:
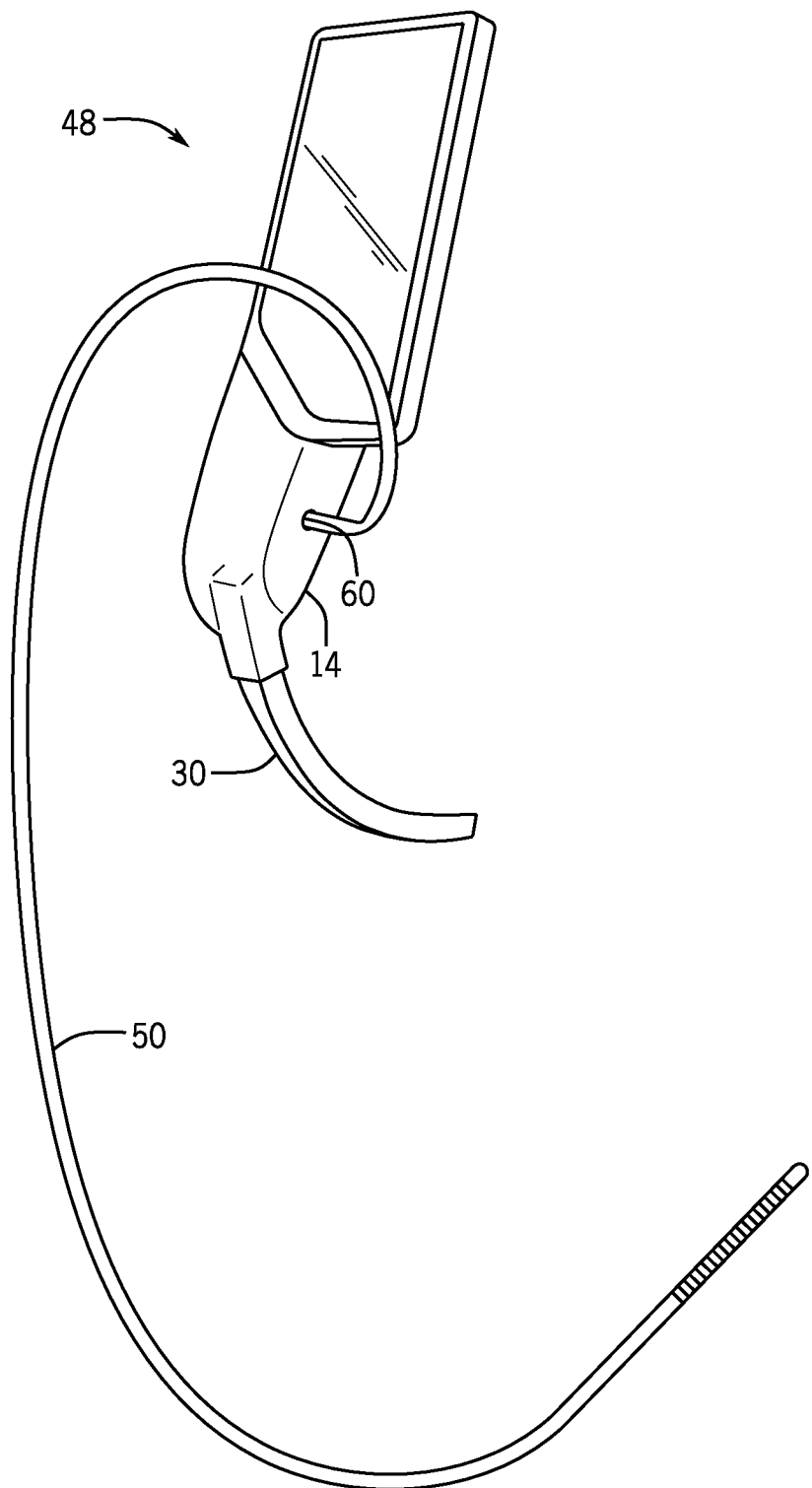
FIG. 21 is a partial perspective view of a multifunctional laryngoscope, in accordance with certain embodiments of the disclosure.
Figure 22:
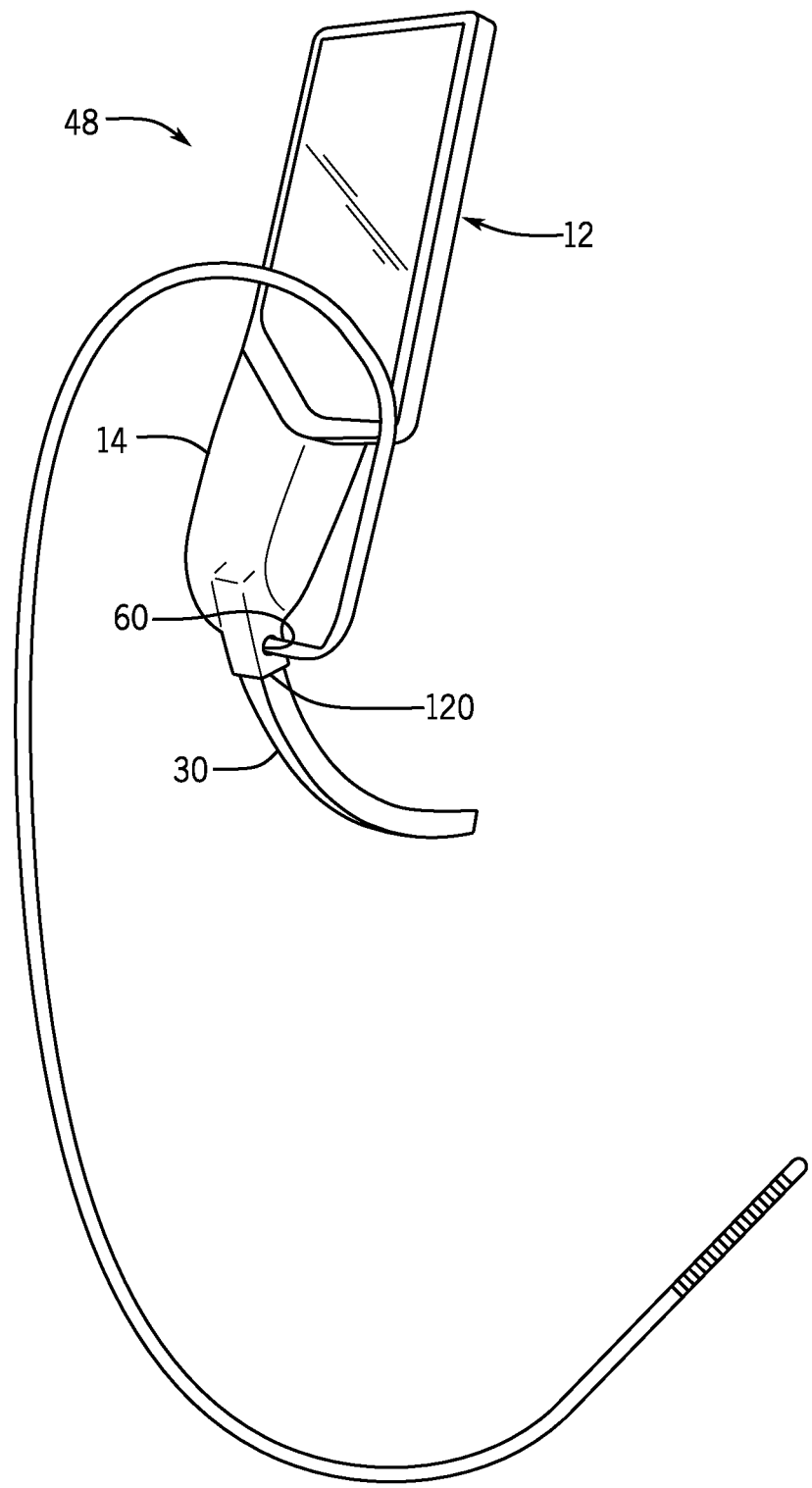
FIG. 22 is a partial perspective view of a multifunctional laryngoscope, in accordance with certain embodiments of the disclosure.

FIG. 20 is a partial perspective view of the multifunctional laryngoscope 12 showing an example that permits attachment of the introducer 50 via one or more implementations of the introducer attachment hub 60. The introducer attachment hub 60 may be implemented as a port facilitating electrical connection of the introducer 50 and may be positioned at a proximal surface 56 of the display screen assembly 20 or, alternatively or additionally, may be positioned on the distal surface 63 of the display screen assembly 20. When a proximal attachment hub 60 and a distal endoscope attachment hub 60 are both present, the multifunctional laryngoscope 12 permits bi-directional attachment of the endoscope 50 at its proximal end 52. In another arrangement, one or more attachment hubs 60 may be available on other portions of a multifunctional visualization instrument 48, such as on the body 14 (see FIG. 21), the camera stick 30, and/or the joint 120 where the camera stick attaches to the body 14 (see FIG. 22). Further, it should be understood that the multifunctional visualization instrument 48 may include multiple attachment hubs 60 to permit the user to select the attachment hub 60 that provides the most comfortable manipulation angle for the introducer relative to the body 14. The coupling of the introducer 50 to an attachment hub 60 activates the functionality of the introducer endoscope camera and/or steering capabilities.

Figure 23:
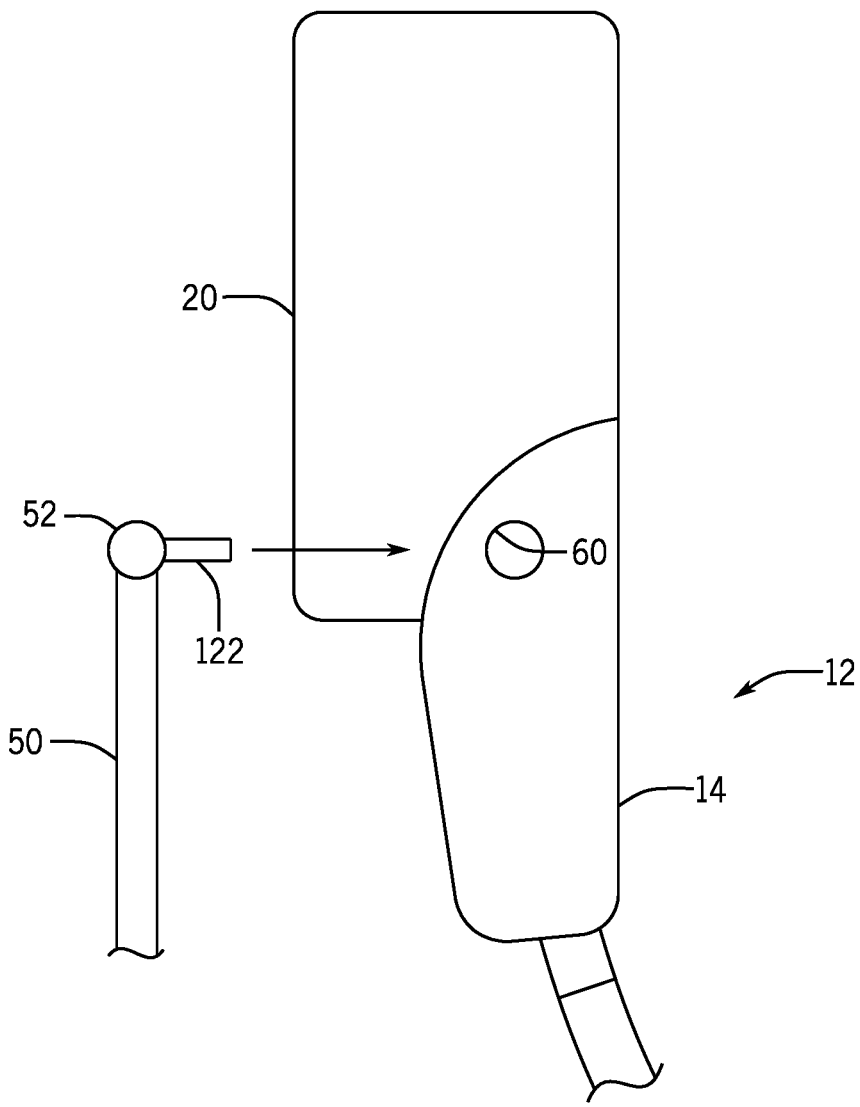
FIG. 23 is a partial perspective view of a multifunctional laryngoscope and introducer, in accordance with certain embodiments of the disclosure.
Figure 24:
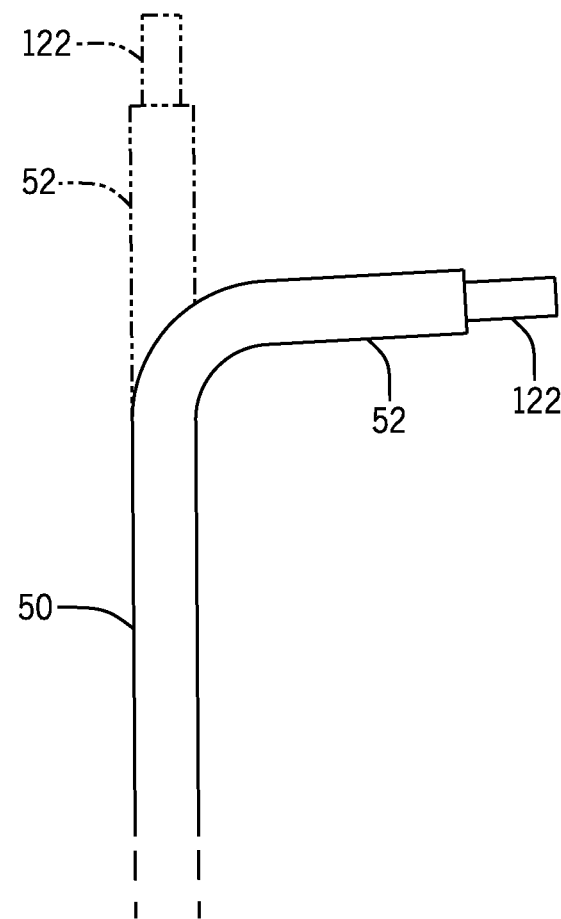
FIG. 24 is a partial perspective view of a proximal end of an introducer, in accordance with certain embodiments of the disclosure.

The attachment hub 60 and/or the introducer 50 may be configured to permit rotation or a change in orientation of the coupled introducer 50 relative to the multifunctional laryngoscope 12 (or control device 57, in some embodiments) to aid manipulation of the proximal end of the introducer 50 while simultaneously acquiring image data and/or while simultaneously steering the introducer 50 into the airway. For example, the user may rotate portions of the introducer 50 away from the display screen 22 to avoid blocking the view of the display assembly 20 to facilitate viewing of the screen without interrupting viewing of the acquired images. FIG. 23 is an embodiment of an introducer 50 implemented with a rotatable prong connector 122 at the introducer's proximal end 52. While coupled via the attachment hub 60, the rotatable prong connector 122 may rotate within the attachment hub 60, enabling the introducer 50 to rotate with respect to the hub 60. The proximal end 52 of the introducer may be capable of straightening or switching between bent and straight configurations as shown in FIG. 24 to permit loading/unloading of an endotracheal tube. The proximal end 52 can be straightened to load or unload the endotracheal tube by sliding it over the straightened introducer, and then the proximal end 52 can be bent again to facilitate connection to the hub 60.

Figure 25:
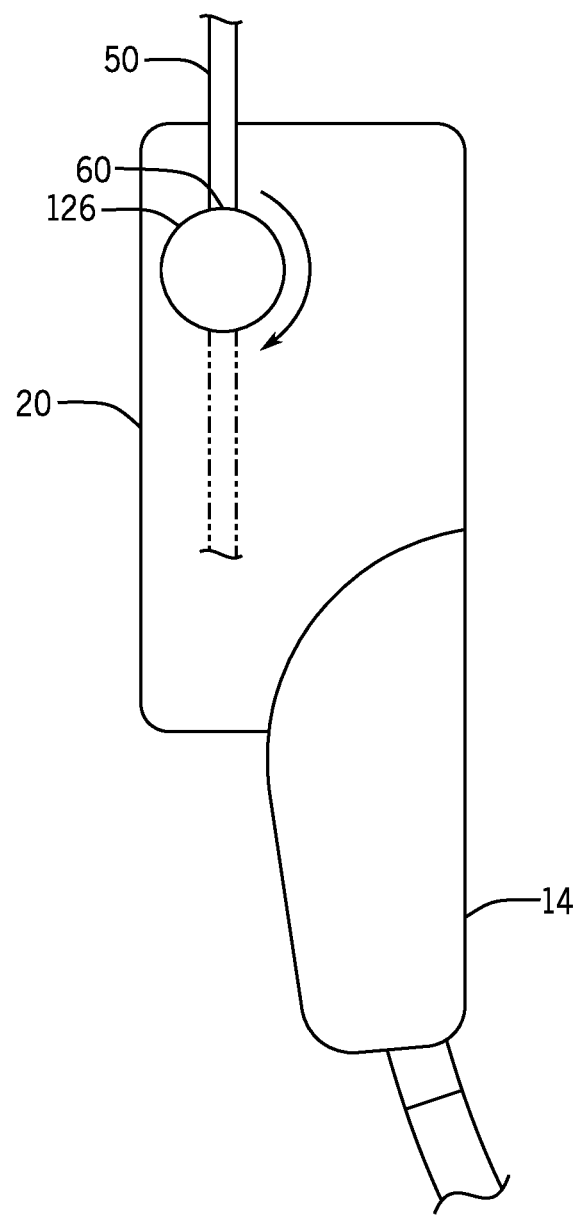
FIG. 25 is a rear partial perspective view of a multifunctional laryngoscope, in accordance with certain embodiments of the disclosure.

FIG. 25 illustrates an arrangement in which the attachment hub 60 is housed in or on a rotatable structure 126. The rotatable structure 126 may be implemented as, for example, a slip ring, a pin-mounted disc, a wheel, or a rotatable rod or barrel-shaped structure. To change an orientation of the introducer 50, the user rotates the rotatable structure 126 to a desired position. In certain embodiments, the rotatable structure 126 may be capable of being locked into place in the desired position and/or angle of the proximal end 52 relative to the multifunctional laryngoscope 12. In one embodiment, the rotatable structure 126 may be capable of being rotated between two or more pre-set positions. That is, the rotatable structure 126 may lock into place at only the two or more pre-set positions when rotated. The rotatable structure 126 and the hub 60 may be disposed on any portion of the multifunctional laryngoscope 12, including on a rear of the display 20 or on the body 14.

Figure 26:
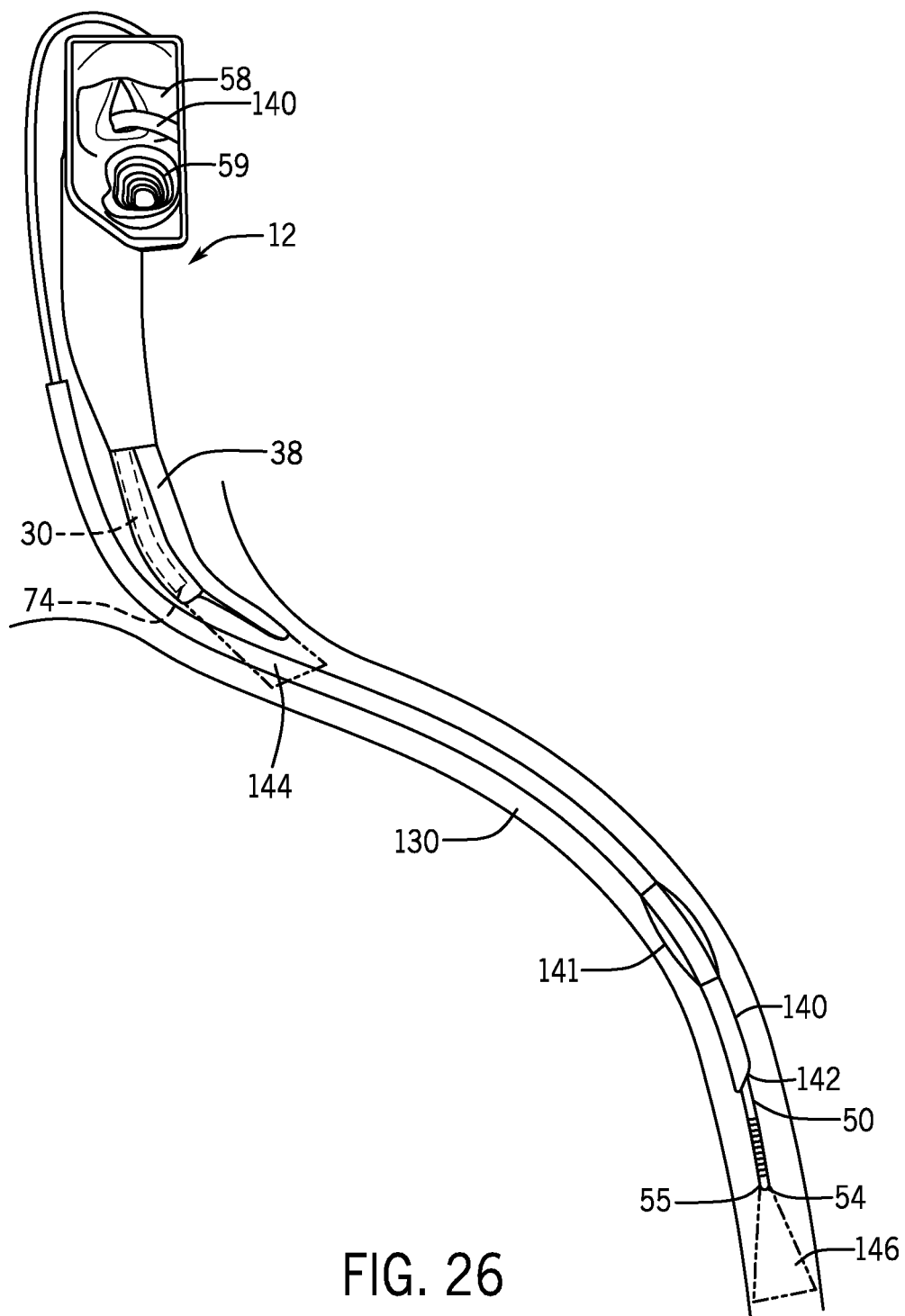
FIG. 26 is a schematic illustration of a multifunctional laryngoscope used in conjunction with an endoscope during intubation with an endotracheal tube, in accordance with certain embodiments of the disclosure.

FIG. 26 is a schematic diagram of an intubation in conjunction with a multifunctional visualization instrument 48, in this case a video laryngoscope, according to an embodiment. To facilitate intubation, the video laryngoscope 12 is inserted into the airway 130 and positioned to view the upper airway. The endoscope introducer 50 is coupled to the video laryngoscope and the multifunctional visualization instrument 48 permits viewing of both the laryngoscope image 58 and endoscope image 59 to permit the user to advance the endoscope introducer 50 to the desired location. This desired location may be a position within the trachea where the endotracheal tube is desired to be placed. While advancing the endoscope introducer 50 through the patient's airway, the user can view both the endoscope image and the laryngoscope image to navigate the endoscope introducer, limit damage to adjacent tissue, and advance the introducer to the desired position. Once the distal end 54 of the endoscope is in the desired position, the endoscope is disconnected from the video laryngoscope 12 (for example, disconnecting the proximal end of the endoscope from the hub 60) to permit an endotracheal tube 140 to be passed over the introducer 50 to facilitate intubation. The depicted embodiment shows an inflatable cuff 141 of the endotracheal tube 140 in a deflated configuration for intubation. However, it should be understood that the depicted intubation protocols may also be used with cuffless endotracheal tubes 140. Once the endoscope is disconnected, in an embodiment, the endoscope image 59 is removed from the display screen, and the laryngoscope image 58 fills the display screen. (Alternatively, the endoscope image may continue to be transmitted to the laryngoscope wirelessly.) The endotracheal tube may then be advanced over the introducer 50 to the desired position in the trachea (e.g., a distal end 142 of the endotracheal tube positioned within the trachea to permit mechanical ventilation via a ventilator coupled to the endotracheal tube), and the user can watch the endotracheal tube in the laryngoscope image 58 on the display 22. Once the endotracheal tube has passed over the proximal end of the introducer 50, the introducer may be re-connected to the laryngoscope and both images presented on the screen, as shown in FIG. 26. Once the endotracheal tube is in position (and secured via inflation of the inflatable cuff 141, if present), the introducer 50 may be withdrawn through the endotracheal tube 140, which remains in place (the distal end 142 remaining where it was placed within the airway). Then, the laryngoscope 12 can also be withdrawn.

As shown in FIG. 26, the laryngoscope camera 74 of the camera stick 30 has a field of view 144 through the blade 38, and the endoscope camera 55 of the endoscope has a field of view 146. The field of view 144 from the laryngoscope camera may enable the medical caregiver to view the upper airway to see the distal end 54 of the introducer 50 as it passes through the upper airway. The field of view 146 from the endoscope camera may enable the medical caregiver to view the lower airways (such as the carina or bronchial tubes), to position the introducer in the location that is desired for the endotracheal tube. During this intubation procedure, the introducer 50 can be connected to the first opening 111 of the hub 60 to orient the introducer in a curved path similar to the curvature of an endotracheal tube. This curvature facilitates placement of the endotracheal tube by passing it over the introducer 50. The acquired laryngoscope image 58 and endoscope image 59 may be displayed during the intubation procedure.

Figure 27:
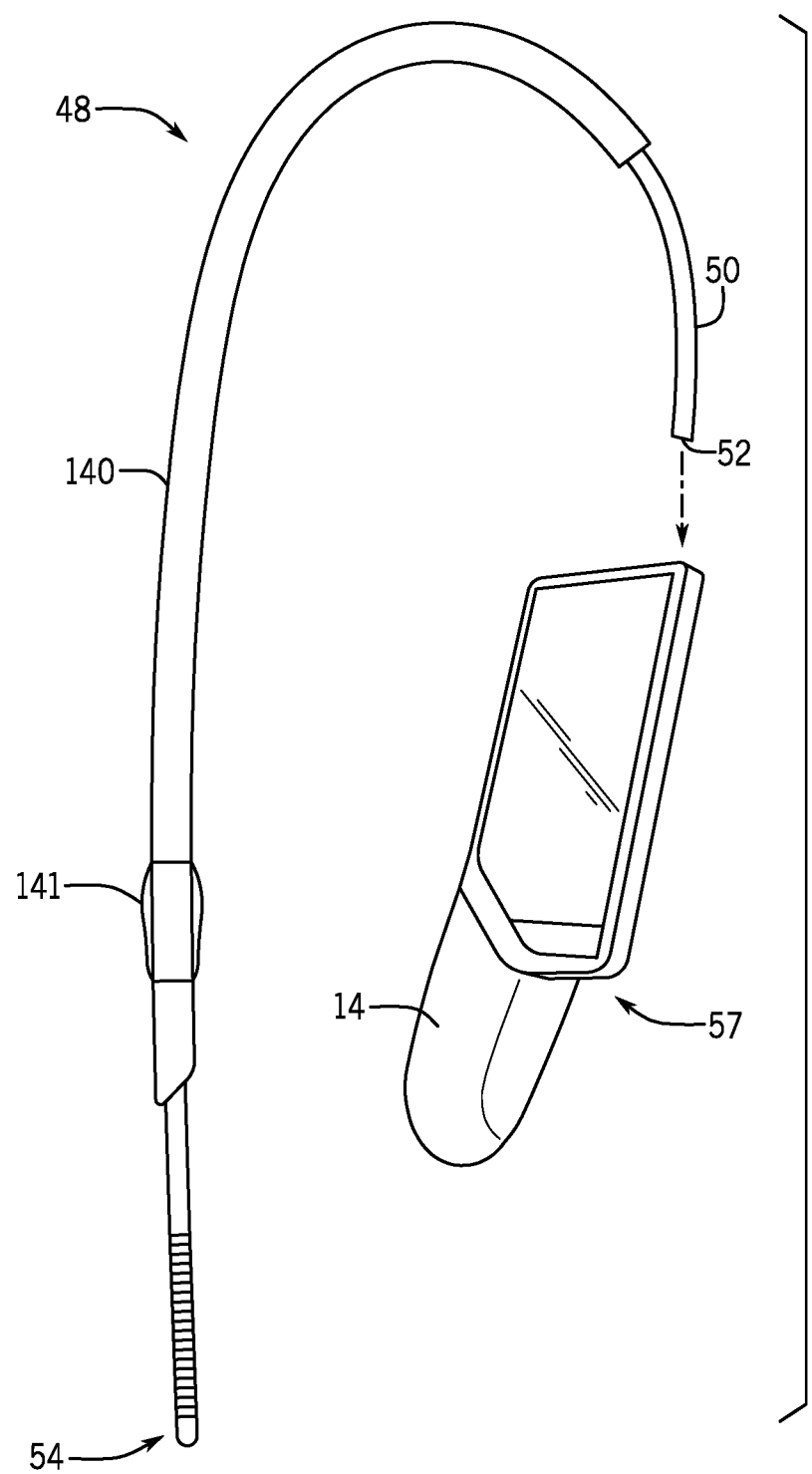
FIG. 27 is a schematic illustration of a multifunctional visualization instrument implemented as a two-part endoscope with an endotracheal tube.

FIG. 27 is a schematic diagram of a multifunctional visualization instrument 48, shown as the control device, puck, or wand 57, reversibly coupled to the introducer 50 with a loaded endotracheal tube 140 including an inflatable cuff 141 in the deflated configuration, according to an embodiment. In contrast to one-piece endoscope devices in which one end of the endoscope is integrally connected to a large controller, screen, handle, or other hub, the two-piece visualization instrument 48 enables the introducer 50 to be detached from the control device 57. As a result, the detached introducer 50 is slim in profile at both the proximal end 52 and the distal end 54, and the endotracheal tube 140 can be loaded onto the introducer 50 from either end. Thus, in an embodiment, the introducer 50 is narrow enough in dimension along its entire length (including both the distal end which may, or may not, have a camera and the proximal end which connects to the wand 57) to pass inside an endotracheal tube. By contrast, with one-piece endoscope devices, the endotracheal tube 140 is typically loaded only from the distal end of the introducer, because the opposite proximal end of the introducer has a screen or control hub that is too large and bulky to pass through an endotracheal tube. The depicted two-piece configuration permits loading of the endotracheal tube 140 from the distal end 54 or the proximal end 52 of the introducer 50.

This configuration is particularly useful during replacement of an existing intubated endotracheal tube. During tube replacement, the introducer 50 is coupled to the control device 57 and is inserted into an endotracheal tube that is already in place in the patient's airway. When the introducer includes a camera, an image from the endoscope camera can be viewed on the control device 57 to facilitate insertion of the introducer 50 into the endotracheal tube. Once the introducer is in position (its distal end at or near the distal end of the endotracheal tube), the introducer is left in place while the proximal end 52 is uncoupled from the control device 57 (such as by disconnecting it from the hub 60). The endotracheal tube 140 may be withdrawn by drawing the endotracheal tube 140 in a proximal direction out of the airway and passing it over the introducer and over the proximal end 52 of the introducer 50. The uncoupling of the introducer and the controller 57 may temporarily interrupt viewing of the airway (absent a wireless connection, for example). However, a new endotracheal tube 140 may then be loaded onto the introducer 50 by passing the new tube in a distal direction over the proximal end 52 while the introducer remains in place in the airway. Once the tube has passed beyond the proximal end 52, that proximal end 52 can be re-coupled to the control device 57 (such as by re-connecting the proximal end 52 to the hub 60) to regain endoscope image on the control device, if desired. Recoupling also allows the control device 57 to regain steering control, if present, of the introducer 50. In this manner, the introducer 50 may not need to be inserted into the airway multiple times to exchange a tube. Instead, tube removal and replacement may be completed while the introducer 50 remains in place in the airway. Further, in one embodiment, during tube exchange the introducer 50 may be coupled to the attachment hub 60 from the bottom opening (i.e., distal coupling 112 as shown in FIG. 19) to promote a desired manipulation angle.

In certain embodiments, an intubation protocol as provided herein may facilitate operator selection between endotracheal tubes 140 of various outer diameters during a patient intubation while also permitting minimally interrupted viewing of the patient airway and one-time positioning of the introducer 50. During intubation, an endotracheal tube 140 of a particular diameter may be selected based on clinician experience and with consideration of patient height, weight, and/or age. However, certain patients may have airways of unpredictable diameters, e.g., narrower relative to typical patients of their size. Further, pediatric patients may have funnel-shaped airways with narrowest points of the funnel being located at a laryngeal exit or the vocal cords, depending on the patient age and growth. Accordingly, an initially-selected endotracheal tube 140 may not be correctly-sized for the patient airway.

If the selected endotracheal tube 140 does not permit intubation after being introduced at least partially into the patient airway, the operator may uncouple the proximal end 52 of the introducer 50 from the control device 57, and withdraw the loaded endotracheal tube 140 from the introducer 50. Subsequently, the operator may reload the introducer 50 with a new endotracheal tube 140 of a different size. Similar to the tube exchange protocol, the introducer 50 may generally remain in place in the airway while endotracheal tubes 140 of one or more different diameters are advanced during intubation and/or intubation attempts. Once the appropriately-sized endotracheal tubes 140 is in place and the patient is successfully intubated, the introducer 50 may be withdrawn. The slim shape of the introducer 50 enables endotracheal tubes to be advanced, removed, and replaced in quick succession, as necessary, to find the tube that is the correct size, without removing the introducer 50 from the airway.

Figure 28:
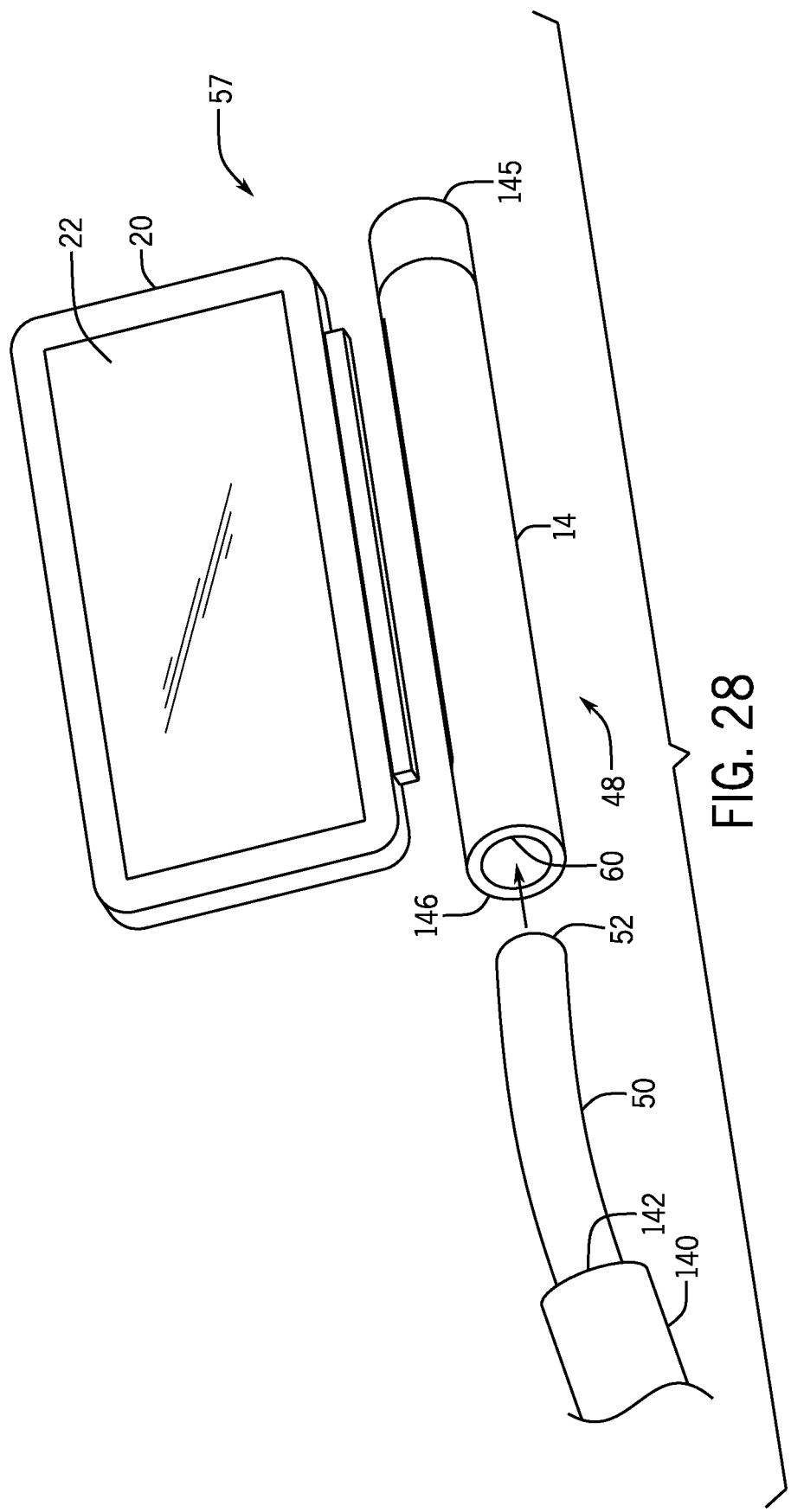
FIG. 28 is a schematic illustration of an in-line multifunctional visualization instrument, in accordance with certain embodiments of the disclosure.

In another embodiment, shown in FIG. 28, the multifunctional visualization instrument 48 is configured as a control device 57 that has a slim, elongate body 14 sized to pass through an endotracheal tube. In the embodiment of FIG. 28, the elongate body 14 is substantially 5 mm in diameter or less, along an axis running from a distal end 145 to a proximal end 146, to permit the endotracheal tube 140 to be slipped over the entire elongate body 14. In operation, this would permit the removal of the endotracheal tube 140 and/or loading of the endotracheal tube 140 without uncoupling of the introducer 50 from the control device 57. In this manner, the manipulation of the introducer 50 is reduced, which may facilitate keeping the distal end in the desired airway position. Further, removing a decoupling step may be beneficial in arrangements in which a single operator is performing the tube exchange. The display assembly 20 and/or the camera stick 30, if present, may be detachable or separate from the elongate body 14, to enable the endotracheal tube to pass over the body 14. Communication with the display assembly is interrupted while it is detached from the body 14, or the display assembly 20 may be configured for wireless communication. Once the endotracheal tube has been passed over the body (in either direction, depending on whether the endotracheal tube is being inserted or removed), the body 14 can be reconnected to the display assembly 20 to resume communication or control that was interrupted.

Figure 29:
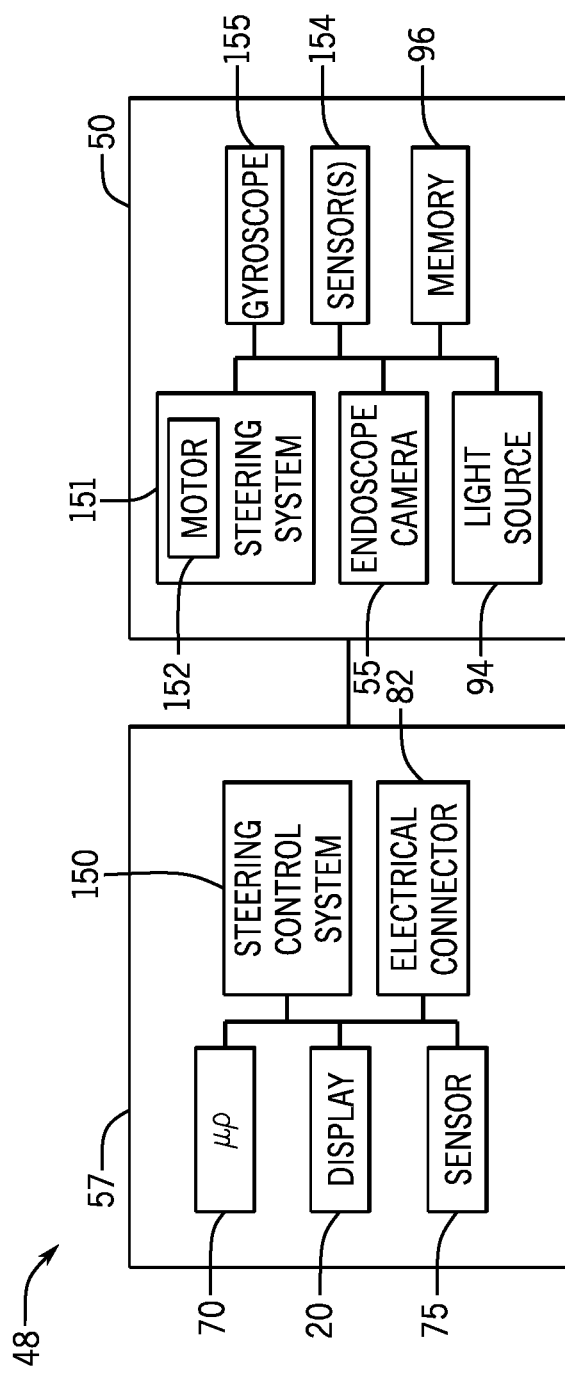
FIG. 29 is a block diagram of a multifunctional laryngoscope system including an endoscope steering system, in accordance with certain embodiments of the disclosure.

As provided herein, the introducer 50 may be configured to be steered via a steering mechanism that permits fine steering of the distal end 54, the endoscope camera 92 (if present), and/or the endoscope light source 94 (if present). FIG. 29 is a block diagram of an embodiment of the multifunctional visualization instrument 48 illustrating the interactions between an introducer steering control system 150 and an introducer steering system 151 that, in certain embodiments, includes a motor 152 that functions to move or rotate the distal end 54 and/or the endoscope camera 55. The steering system may include one or more memory metal components (e.g., memory wire, Nitinol wire) that changes shape based on electrical input, a piezoelectric actuators (such as the SQUIGGLE motor from New Scale Technologies, Victor NY), a retractable sheath (retractable to release a pre-formed curved component such as spring steel which regains its curved shape when released from the sheath), or other means for bending, rotating, or turning the distal end or components at the distal end of the introducer. In certain embodiments, to permit the user to control the system 48 with two hands and without additional assistance (one hand gripping the laryngoscope and the other hand gripping the introducer), the steering control 150 may be operated via the laryngoscope display screen 22, e.g., via the touch surface of the display screen itself, or a separate touch or mechanical sensor 75.

Figure 30:
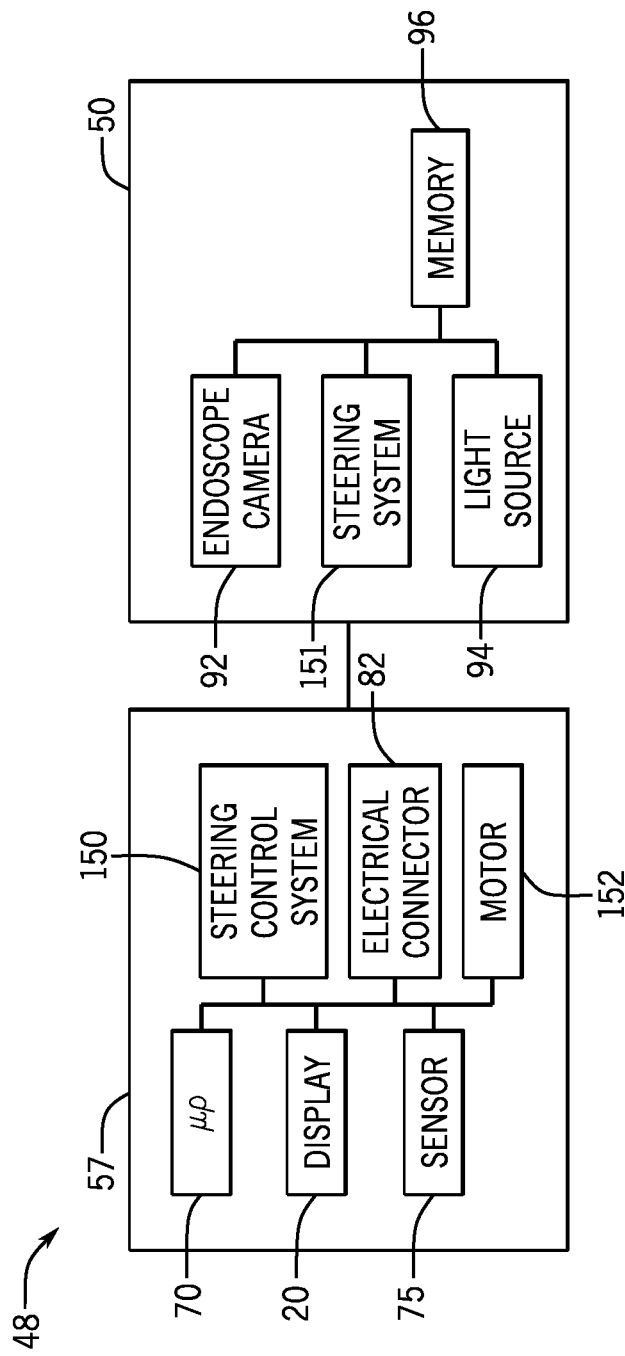
FIG. 30 is a block diagram of a multifunctional laryngoscope system including an endoscope steering system, in accordance with certain embodiments of the disclosure.

In certain embodiments, the introducer 50 may be configured to be a relatively simple, inexpensive disposable device. For example, certain steering components of the multifunctional visualization instrument 48 may be resident in the reusable control device 57 rather than the introducer 50. FIG. 30 is a block diagram of an embodiment of the multifunctional visualization instrument 48 illustrating the motor 152 being housed within the control device. The motor 152 and the endoscope steering control system 150 may be coupled to and provide control to the endoscope steering system 151 via the electrical connector 82. As illustrated, the motor 152 and the motor drive function may be housed within the control device 57, e.g., within the body 14, where more space is available relative to the introducer 50. Such an arrangement may also facilitate providing a thinner introducer 50. In an example, the motor 152 may drive a mechanical pull wire system of the introducer 50. The multifunctional visualization instrument 48 may be configured to pass the drive from the body 14, e.g., via a removable introducer cable or connector (which may also be configured to be in-line). Placing the motor 152 within the body 14 may permit a slimmer, high torque, faster response and lower cost introducer 50.

The endoscope introducer 50 may also include one or more on-board sensors 154 that provide feedback to the processor 70, whereby the feedback in turn is used to adjust one or more characteristics of the display 20. In one embodiment, the sensor 154 is an accelerometer or angular velocity sensor that senses a change in orientation of the endoscope camera 55 relative to a reference orientation. The processor 70 may use feedback from the sensor 154 and automatically adjust the displayed image to a desired orientation. For example, a gyroscope 155 may be included at a distal end of the endoscope 50, which may track changes in steering caused by input to the user controls. As a result of signals from the gyroscope 155, the image displayed on the display 20 may be adjusted to make sure that the upward direction (anterior, toward the patient's chest) remains upward (toward the top proximal surface 56) on the display screen 22, even when the endoscope 50 is rotated or turned inside the patient. Referring to FIG. 5 as an example, the image on the display screen 22 comes from the endoscope camera. As an example, the user may rotate the endoscope 50 counterclockwise 90 degrees (or any amount), such as to better position the endoscope 50 within the patient's anatomy. In this embodiment, the image on the display screen 22 in FIG. 5 remains stationary, even when the endoscope 50 is rotated. The gyroscope 155 at the tip or distal end 54 of the endoscope 50 registers the 90-degree rotation, and the microprocessor 70 rotates the image on the screen in the reverse direction (in this example, counter-clockwise) by the same amount (90 degrees). If the endoscope 50 is rotated again, in either direction, the microprocessor 70 again compensates, so that the image on the screen 22 remains oriented with the patient's anterior pointed upward on the display screen 22. In another embodiment, the microprocessor 70 receives realtime signals from the gyroscope 155 indicating the relationship between the camera and gravity, so that the microprocessor 70 can continually adjust the image to keep the direction of gravity pointed downward on the laryngoscope display screen 22, even as the endoscope 50 itself is rotated.

Further, the processor 70 may use feedback from one or more of the camera 55, the camera 74 (see FIG. 6), or one or more sensors 154 to adjust the displayed image to a desired orientation. In one example, the image data (e.g., the introducer image) from the introducer camera 55 is provided to the processor 70, which in turn process the image data and uses image recognition to determine a position of the introducer distal end 54 based on shape or size characteristics of the portions of the airway recognized from the image data. For example, the microprocessor 70 may be programmed to identify vocal cords in an image from the endoscope camera 55. Feedback from the gyroscope 155 may provide additional information as to the orientation of the introducer distal end 54 within the passage. With image recognition and/or gyroscope input, the microprocessor 70 can identify the anterior direction within the image, and orient the image on the laryngoscope display screen 22 such that the anterior direction is maintained toward the top of the laryngoscope display screen 22.

In a further example, the orientation of the image may actually be flipped during a procedure, such as during a nasal intubation. During nasal intubation, a top side of the endoscope 50 is initially toward the patient's anterior, but as the endoscope 50 is advanced through the nasal passages and into the throat, the top side of the endoscope 50 is now toward the patient's posterior. In an embodiment, the microprocessor 70 orients the image on the display screen 22 such that the patient's anterior is maintained toward the top of the screen 22, even as the endoscope 50 flips from anterior to posterior. The anterior direction can be identified by a recognized position of the introducer distal end 54 in the nasal cavity or the nasopharynx, e.g., based on passage size and shape as resolved from the image data, together with orientation information as determined from the data provided by the gyroscope 155. This information may be used to display the image from the camera 55 on the display 20 in a first orientation (e.g., a rotated orientation, with a first side of the endoscope pointed "up" in the display) that is more intuitive for the operator navigating within the nasopharynx (such as keeping the patient's anterior pointed "up" in the display). As the introducer distal end 54 passes into the trachea and flips over, the image from the camera 55 may be displayed on the display 20 in a second orientation (e.g., an unrotated orientation, with the same side of the endoscope now pointed "down" in the display) that is more intuitive for the operator navigating within the trachea (again keeping the patient's anterior pointed "up" in the display). The difference in orientation between the first and second orientations may be 90 degrees or 180 degrees. In another embodiment, the rotation may further be determined based on changes in orientation of the distal end 54 per gyroscope 155 feedback.

Figure 31:
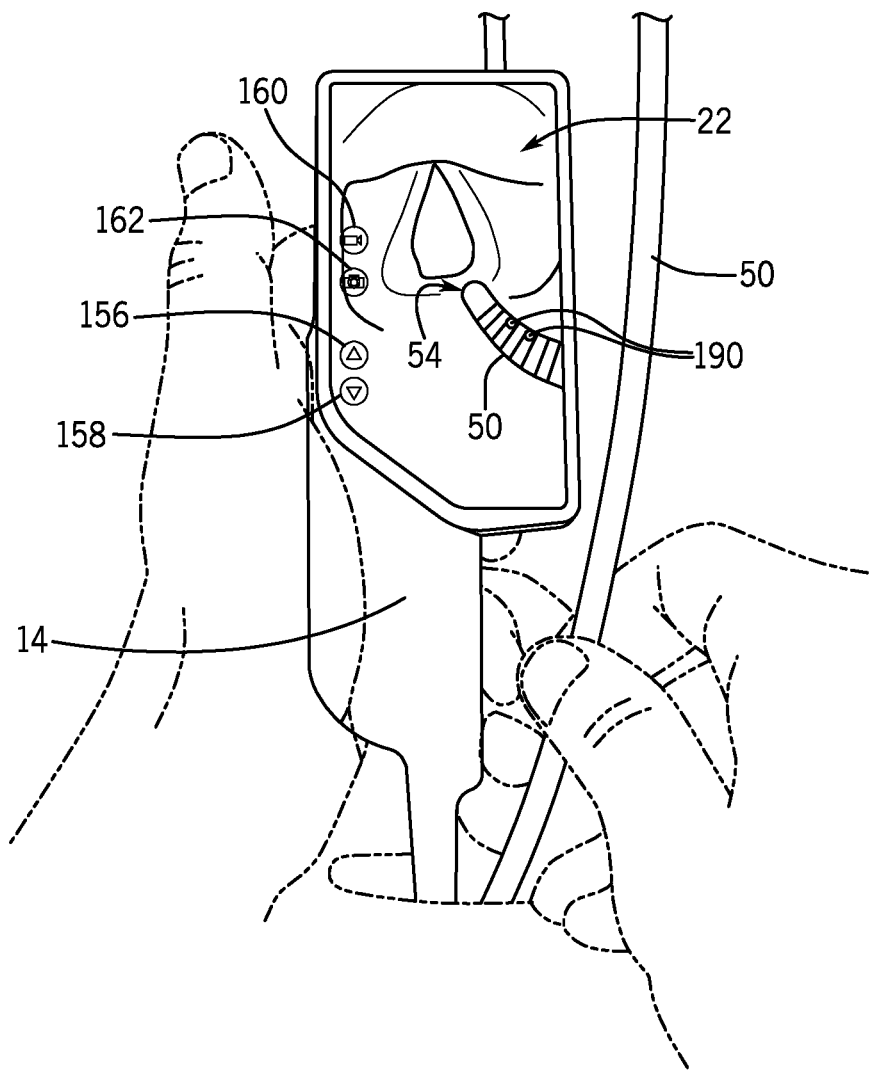
FIG. 31 is a schematic illustration of a multifunctional laryngoscope display used in conjunction with a steerable introducer, in accordance with certain embodiments of the disclosure.

FIG. 31 shows an example display screen 22 displaying indicators for steering inputs from a user, shown as up arrow 156, and down arrow 158, for steering the articulating introducer 50. In the illustrated embodiment, the user is able to achieve fine steering of the introducer 50 with one hand by pressing the appropriate arrows 156, 158, e.g., with just the motion of the thumb. The steering input received via the arrows 156, 158 on the display screen 22 is communicated to the endoscope steering control system 150, which in turn drives the motor 152 (see FIG. 29) (or other steering mechanism) according to the user's instructions. In this manner, the multifunctional laryngoscope facilitates active steering of the introducer 50 without sacrificing single user two-handed operability. The user may steer the distal tip of the introducer and its associated endoscope camera 55 (if present) via touch input on the display screen that can be performed with a thumb motion so that the user can steer the introducer and maintain the desired grip and angle on the laryngoscope 12 with one hand, while simultaneously advancing the introducer 50 with the other hand. While the depicted embodiment shows arrows 156, 158, it should be understood that other user input motions are contemplated, such as a swipe motion (e.g., swiping in a clockwise motion to turn right or in a counterclockwise motion to turn left, swiping up to turn up or swiping down to turn down). Other contemplated user inputs may include tapping, double tapping, etc. Further, the displayed indicators may be any appropriate icon or symbol. As shown in FIG. 31, the distal end 54 of the introducer 50 is visible on the display screen 22, within the field of view of the laryngoscope camera. As shown in FIG. 31, the distal end 54 is curving upwardly (in the image), based on steering inputs from the user.

Figure 32:
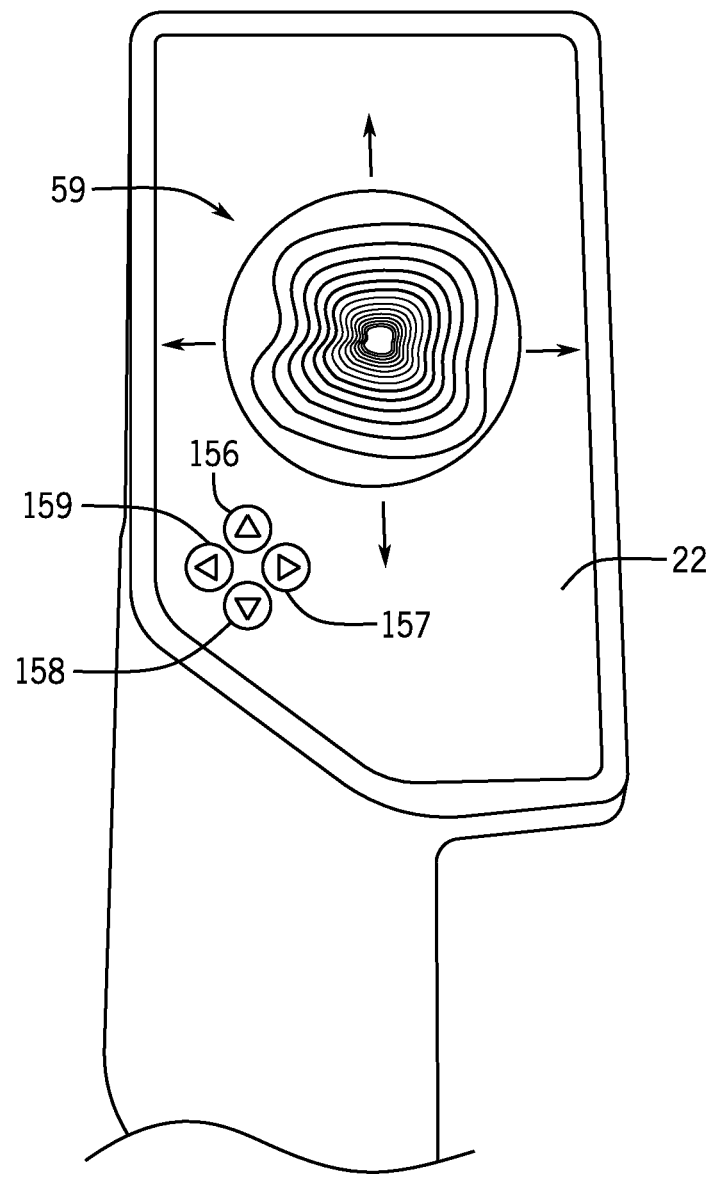
FIG. 32 is a schematic illustration of a multifunctional laryngoscope display that may be used in conjunction with a steerable introducer, in accordance with certain embodiments of the disclosure.

In an embodiment, the introducer 50 shown in FIG. 32 is a blind articulating bougie that does not include a camera and does not provide any image data back to the laryngoscope display screen 22. However, the distal tip 54 of the bougie is actively steerable (by a steering mechanism as described above) in order to steer the bougie through the patient's anatomy, such as bending the tip 54 up or down to steer the bougie around a mass or through an opening. The ability to steer the bougie can be particularly useful during intubation, to bend the tip 54 in an upward direction in order to pass the tip through the vocal cords (when the patient is lying supine). Thus, in an embodiment, the blind articulating bougie 50 is electrically coupled to the laryngoscope (such as the hub 60) so that drive signals from the laryngoscope can be passed to the bougie to steer it. The user can input instructions to steer the bougie by touching the arrows 156, 158 as discussed above. In an embodiment, the bougie is steerable in only two directions (for example, up and down, in a two-dimensional plane). In another embodiment, the bougie is steerable in additional directions (for example, up, down, left, and right). The control inputs may also include a video icon 160 and/or a still image icon 162 that permit the operator to capture still image and/or video. Additionally, in an embodiment, the bougie includes a visible indicia or marker 190 that indicates to the user which direction is up for the steering controls. When the user presses the up arrow 156, the bougie bends upward in the direction of the marker 190. The marker 190 can be formed by printed graphics, a groove or other three-dimensional feature, a glow-in-the-dark ink or indicia, or an actively powered light (such as a small LED strip or light as shown).

FIG. 32 shows an alternate embodiment in which arrows are used to steer the endoscope camera 55. In this embodiment, the screen includes right and left arrows (arrows 157, 159). An additional benefit of the present disclosure is fine steering of the endoscope camera 55 using only touch screen or single finger user inputs. The user, while viewing the endoscope image 59 on the display screen 22, can adjust the angle of the endoscope camera 55 in an intuitive and natural manner. Tapping the up arrow 156 adjusts the endoscope camera 55 to tilt up, etc. The orientation change may be viewed in real time, permitting the user to achieve a desired orientation while holding the endoscope introducer 50 at the desired position within the airway.

Figure 33:
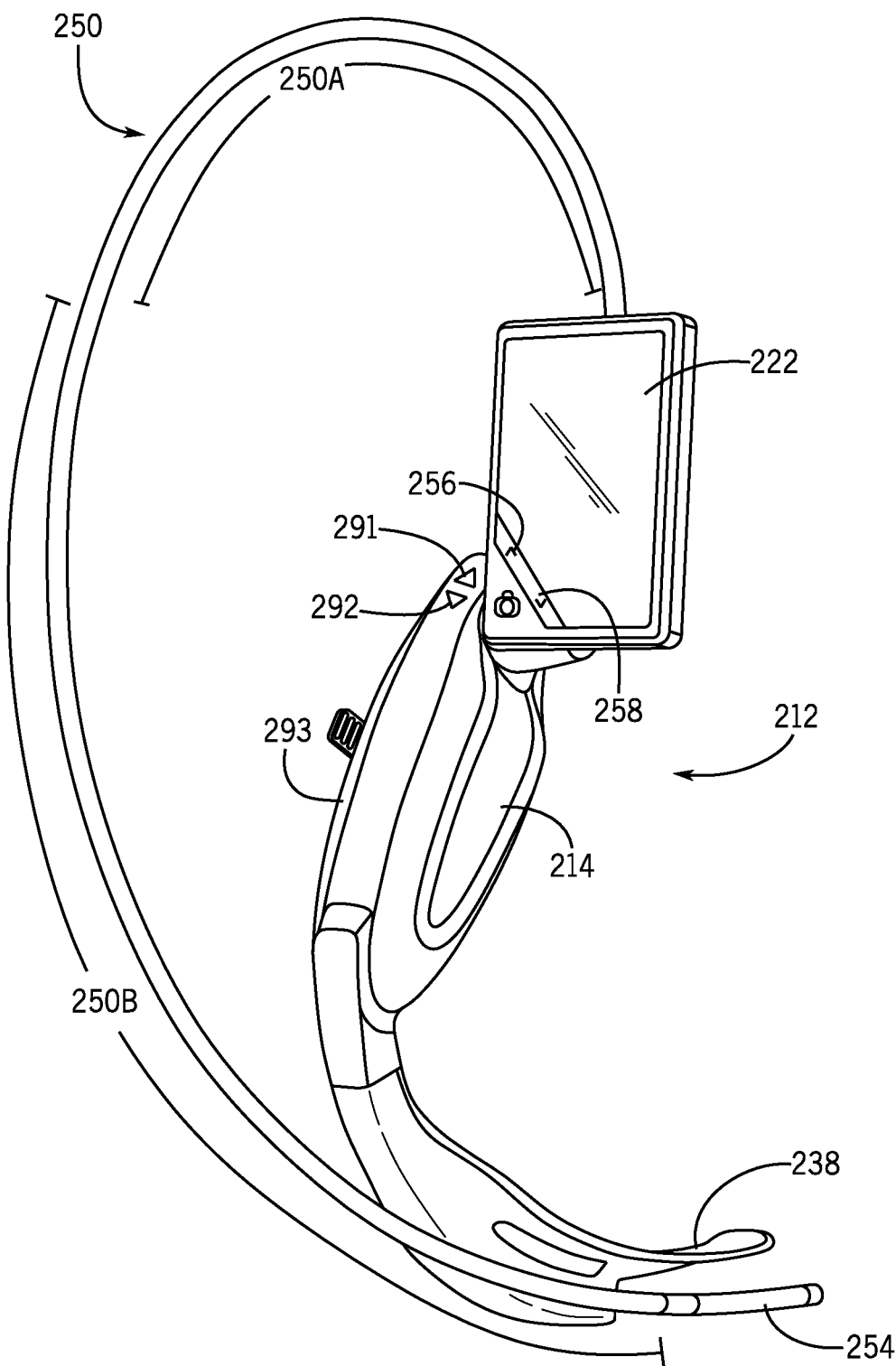
FIG. 33 is a front perspective view of a video laryngoscope coupled to an articulating introducer, in accordance with certain embodiments of the disclosure.

The controls that the user accesses to steer the introducer (such as a blind bougie or endoscope with camera) can be touch icons on the screen, such as the arrows 156 and 158 in FIGS. 31-32, or they can be other buttons or sensors located on the laryngoscope, such as mechanical buttons 291, 292 as shown in FIG. 33. This figure shows a laryngoscope 212 coupled to a blind articulating bougie 250, which couples to the laryngoscope at a port on the rear surface of the laryngoscope display screen 222 (such as with a hub 60 as described above). The distal end 254 of the bougie is actively steerable, and the user can give instructions to steer the bougie by pressing the up button 291 or the down button 292. These mechanical buttons (which could be capacitive touch sensors or moving buttons) are located on the body 214 of the laryngoscope. In an embodiment, in addition to the buttons 291 and 292, touch arrows 256 and 258 are also shown on the display screen 222, and the user can use any of these inputs to steer the bougie 250. Additionally, other buttons may be provided for other features of the bougie, such as to activate a suction feature if a suction channel is provided in the bougie, or to activate a light on the bougie.

In the embodiment of FIG. 33, a portion 293 of the body 214 is removable, such as a removable lid to a battery compartment, or as part of the removable battery itself, which is discarded and replaced with a new one. In an embodiment, the buttons 291, 292 are located on this removable portion 293, such that the functionality of the buttons 291, 292 can be added to existing laryngoscopes simply by replacing the replaceable portion 293 with one that has buttons, such as by replacing the battery. In an embodiment, an existing laryngoscope that does not include any buttons for bougie steering can be retrofitted to include buttons by a software update to add buttons on the screen 222 and/or replacing the portion 293 to add buttons 291, 292 on that portion.

In an embodiment, the bougie 250 has variable stiffness along its length. For example, a first proximal segment 250A is relatively stiffer compared to a second segment 250B (which is distal to the first segment 250A). For example, the first segment 250A can include a bendable metal insert, like a stylet, that gives some resistance to bending and then retains its bent shape, such as the curved shape shown in FIG. 33. An endotracheal tube can be pre-loaded onto the segment 250A before the introducer 250 is inserted into the patient. The second segment 250B is relatively less stiff, such as a hollow flexible tube without a metal insert. The distal end 254 may be even more flexible, such as a steerable silicon tip. This variable stiffness is helpful to retain a pre-loaded endotracheal tube along the proximal segment 250A, such that a single caregiver can then grip and insert the laryngoscope 212 with the left hand, advance the introducer 250 with the right hand to the desired location, and then use the right hand to pass the pre-loaded endotracheal tube over the introducer 250 into the patient.

In an embodiment, the distal end 254 of the blind articulating bougie 250 is a removable tip that can be removed and replaced with other types of tips, such as tips with a different shape, different steering mechanisms, or different tools (such as a biopsy needle or ablation pad). The features of the laryngoscope 212 and blind bougie 250 described above and shown in FIG. 33 can also be used with an endoscope introducer that carries a camera at its distal end.

In certain embodiments, the steering user inputs are displayed in conjunction with coupling of the appropriate introducer 50, e.g., an introducer 50 with articulated steering. For example, coupling via the attachment hub 60 causes identification or configuration information stored in the memory 96 of the introducer 50 to be accessed to cause the display screen 22 to display the appropriate steering user inputs. If the endoscope is not configured for such steering, the display screen 22 may revert to a default setting without displaying the steering inputs.

In certain embodiments, one or both of the laryngoscope blade 38 or introducer 50 are single use devices. The user couples the single use laryngoscope blade 38 or introducer 50 to the multifunctional instrument 48 and, after use, disposes of the used laryngoscope blade 38 and introducer 50 to prevent cross-contamination between patients, to maintain cleanliness of the camera stick 30, and to facilitate use of sterilized components. In particular embodiments, the entire introducer 50, including the camera 55, is disposable. Accordingly, the laryngoscope 12 may be configured to assess whether one or both of the laryngoscope blade 38 or introducer 50 have been previously used to prevent re-use of contaminated components and to augment compliance procedures. In certain embodiments, the assessment may account for detachment of the introducer 50 during tube exchanges and may allow a certain number of disconnections and reconnections that are associated with or characteristic of typical tube exchange patterns. For example, such disconnections and reconnections may be associated with connection of a valid introducer 50 if they occur within a preset time period (e.g., 1 hour) measured from or compared to a time stamp associated with an initial connection of the introducer 50. Later disconnections and reconnections of the same introducer 50 (e.g., outside of the preset time period) may trigger warnings or other indicators.

In addition, the multifunctional instrument 48 may be configured to recognize what type of laryngoscope blade 38 or introducer 50 is attached. Further, the camera stick 30 may be used capture images of and visually recognize the type of laryngoscope blade 38 attached, the type/size endotracheal tubes passing by, introducer types, etc. For example, images of the markings on the tube, introducer, and/or blade, or existing or dedicated (machine seeable) markings addable to tubes/introducers/blades may be captured and used by the processor of the multifunctional instrument 48 to recognize associated devices. In addition, the images may capture depth markings to provide information about introducer depth.

Figure 34:
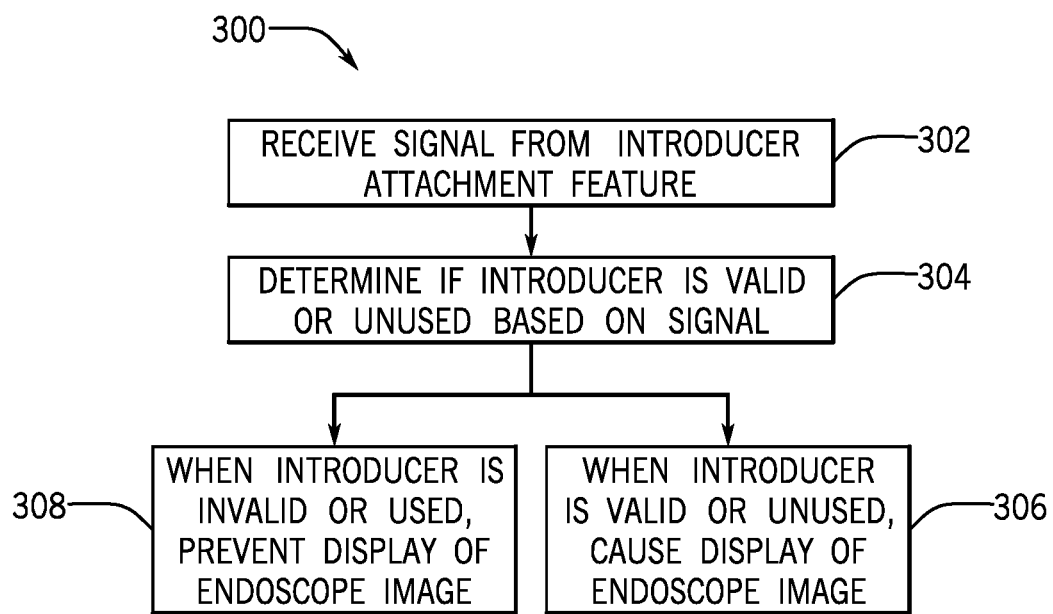
FIG. 34 is a flow diagram of a multifunctional laryngoscope display control technique, in accordance with certain embodiments of the disclosure.

FIG. 34 is a flow diagram of a method 300 of validating a coupled introducer 50. One or more steps of the method 300 may be performed by the laryngoscope 12, e.g., via instructions stored in the memory 72 and executed by the processor 70 (see FIG. 6). The introducer coupling is detected via a signal from the introducer attachment hub 60 (block 302). The signal is assessed to determine if the introducer is valid or unused based on the signal (block 304). For example, in one embodiment, the laryngoscope 12 may write information to the memory 96 of the introducer 50 when coupled to the laryngoscope 12 to indicate that the introducer 50 has been previously used. If that introducer 50 is decoupled and then used again, the laryngoscope 12 accesses or reads the memory 96 and determines that the introducer 50 has been previously used based on the information accessed from the memory 96. In another embodiment, an introducer 50 may be reused if properly cleaned and sterilized if the memory 96 stores a code indicative of cleaning.

In yet another embodiment, the laryngoscope 12 may be configured to detect inappropriate endoscope introducers 50. For examples, a user may select a non-bronchial or non-tracheal endoscope introducer 50. If the endoscope does not have the appropriate identification information stored in the memory 96, the introducer 50 may be deemed invalid. When a valid or unused introducer 50 is coupled, the laryngoscope 12 causes display of the endoscope images (block 306). However, when an invalid or used endoscope is coupled, the laryngoscope 12 may prevent display of the endoscope images (block 308). In other embodiments, a user may be permitted to override the block of endoscope image display via a user input.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A visualization instrument system, comprising:
    an introducer comprising an articulating distal end and at least one steering wire;
    a laryngoscope handle, comprising;
        a body;
        a display screen mounted to the body;
        a camera coupled to a distal end of the body; and
        a port configured to mate with the introducer to removably couple the introducer to the laryngoscope handle and communicate steering controls between the laryngoscope handle and the introducer to articulate the articulating distal end of the introducer via the at least one steering wire; and
        a laryngoscope blade enclosing the camera within a channel of the laryngoscope blade.

2. The system of claim 1, comprising an endotracheal tube disposed about the introducer.

3. The system of claim 1, wherein the port is disposed on a rear surface of a housing of the display screen.

4. The system of claim 1, comprising one or more steering inputs configured to receive user input to generate the steering controls.

5. The system of claim 1, wherein the introducer comprises an introducer camera providing an introducer image to the display screen, and further comprising an angular velocity sensor, wherein a display characteristic of the introducer image is based on a signal from the angular velocity sensor.

6. The system of claim 5, wherein the display characteristic comprises an orientation of the introducer image.

7. The system of claim 1, wherein the port comprises an opening that receives a proximal end of the introducer.

8. The system of claim 1, wherein the introducer comprises a connector that mates with an electrical connector of the port.

9. The system of claim 8, wherein the laryngoscope handle comprises a processor that receives a signal from the electrical connector of the port indicative of mating with the connector of the introducer.

10. The system of claim 9, wherein the signal causes the system to switch from a laryngoscope operating mode to a multifunctional visualization instrument operating mode.

11. The system of claim 10, wherein the multifunctional visualization instrument operating mode causes display of an image from the camera and an introducer image from the introducer.

12. The system of claim 9, wherein the signal is indicative of a presence of a working channel of the introducer.

13. A visualization instrument system, comprising:
    an introducer comprising an articulating distal end and at least one steering wire; and
    a laryngoscope handle, comprising;
        a body;
        a display screen mounted to the body;
        a camera coupled to a distal end of the body; and
        a connector configured to mate with the introducer to removably couple the introducer to the laryngoscope handle and communicate steering controls between the laryngoscope handle and the introducer to articulate the articulating distal end of the introducer via the at least one steering wire.

14. The system of claim 13, comprising an endotracheal tube disposed about the introducer.

15. The system of claim 13, wherein the connector is disposed on a rear surface of a housing of the display screen.

16. The system of claim 13, comprising one or more steering inputs configured to receive user input to generate the steering controls.

17. The system of claim 13, wherein the introducer comprises an introducer camera providing an introducer image to the display screen, and further comprising an angular velocity sensor, wherein a display characteristic of the introducer image is based on a signal from the angular velocity sensor.

18. The system of claim 13, wherein the laryngoscope handle comprises a processor that receives a signal from the connector indicative of mating with the introducer.

19. The system of claim 18, wherein the signal causes the system to switch from a laryngoscope operating mode to a multifunctional visualization instrument operating mode.

20. The system of claim 18, wherein the signal is indicative of a presence of a working channel of the introducer.

* * * * *